(12) United States Patent
Yaoka et al.

(10) Patent No.: US 10,907,334 B2
(45) Date of Patent: Feb. 2, 2021

(54) SANITARY WASHING DEVICE

(71) Applicant: TOTO LTD., Kitakyushu (JP)

(72) Inventors: Toshinari Yaoka, Kitakyushu (JP);
Minoru Sato, Kitakyushu (JP);
Keisuke Tashiro, Kitakyushu (JP);
Satoru Matsumoto, Kitakyushu (JP);
Shogo Kanda, Kitakyushu (JP)

(73) Assignee: TOTO LTD., Fukuoka (JP)

( * ) Notice: Subject to any disclaimer, the term of this patent is extended or adjusted under 35 U.S.C. 154(b) by 0 days.

(21) Appl. No.: 16/412,752

(22) Filed: May 15, 2019

(65) Prior Publication Data

US 2019/0368180 A1 Dec. 5, 2019

(30) Foreign Application Priority Data

Jun. 1, 2018 (JP) .................................. 2018-106365
Mar. 29, 2019 (JP) .................................. 2019-067934

(51) Int. Cl.
| | |
|---|---|
| *E03D 9/08* | (2006.01) |
| *B05B 15/555* | (2018.01) |
| *A47K 7/08* | (2006.01) |
| *A61L 2/10* | (2006.01) |
| *E03D 9/00* | (2006.01) |

(52) U.S. Cl.
CPC .................. *E03D 9/08* (2013.01); *A47K 7/08* (2013.01); *A61L 2/10* (2013.01); *B05B 15/555* (2018.02); *E03D 9/002* (2013.01)

(58) Field of Classification Search
CPC ...................................................... E03D 9/08
USPC .............................................. 4/420.1–420.5
See application file for complete search history.

(56) References Cited

U.S. PATENT DOCUMENTS

2007/0256226 A1   11/2007   Pinizzotto

FOREIGN PATENT DOCUMENTS

| CN | 101225942 A | 7/2008 |
|---|---|---|
| JP | 2006-274641 A | 10/2006 |
| JP | 2008-196141 A | 8/2008 |
| KR | 2009-0098644 A | 9/2009 |
| WO | 2016/129394 A1 | 8/2016 |

OTHER PUBLICATIONS

Extended European Search Report for Application No. 19177247.4, dated Oct. 7, 2019.
English translation for Japanese Publication No. 2013-083141A dated May 9, 2013 in the name of Kwareukyutar Co. Ltd.

*Primary Examiner* — Lori L Baker
(74) *Attorney, Agent, or Firm* — Pearne & Gordon LLP

(57) ABSTRACT

A sanitary washing device includes a nozzle, a drive device, a casing, a nozzle lid, and an illuminator. The casing includes a nozzle container. The nozzle lid is provided to be openable and closable with respect to an opening provided at a front end of the nozzle container. The nozzle lid is in a closed state in which the opening is closed when the entirety of the nozzle is stored in the nozzle container. The illuminator irradiates sterilizing light into an interior of the nozzle container. The sterilizing light has a sterilizing effect. At least one of the nozzle lid or a vicinity of the nozzle lid is luminous in a state of being visible to the user when the nozzle lid is in the closed state and the sterilizing light from the illuminator is irradiated into the interior of the nozzle container.

20 Claims, 13 Drawing Sheets

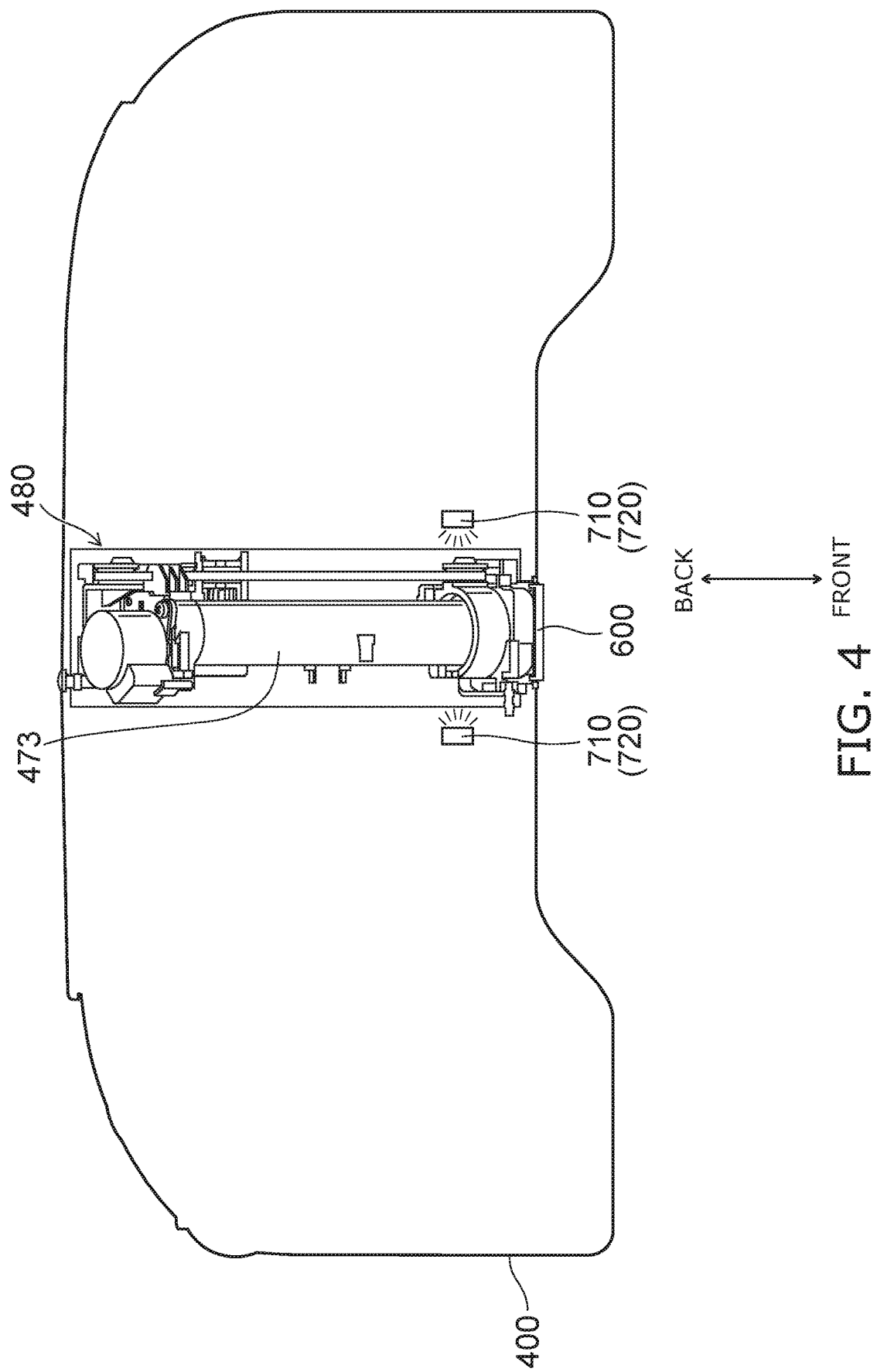

SANITARY WASHING DEVICE

CROSS-REFERENCE TO RELATED APPLICATIONS

This application is based upon and claims the benefit of priority from Japanese Patent Application No. 2018-106365, filed on Jun. 1, 2018 and No. 2019-067934, filed on Mar. 29, 2019; the entire contents of which are incorporated herein by reference.

FIELD

Embodiments described herein relate generally to a sanitary washing device.

BACKGROUND

To remove dirt adhered to a private part wash nozzle, technology is discussed in Patent Literature 1 in which ultraviolet light (UV light) having a sterilizing effect is irradiated on the private part wash nozzle.

A nozzle container that stores the private part wash nozzle may be provided at the periphery of the private part wash nozzle; and a nozzle lid for suppressing the penetration into the nozzle container of urine or the like may be provided at an opening at the front end of the nozzle container. In such a case, the nozzle container and the like also can be sterilized by irradiating the ultraviolet light on the nozzle container and the like when irradiating the ultraviolet light on the private part wash nozzle.

However, because the nozzle lid is provided at the opening of the nozzle container, in order for the user to directly confirm that the nozzle container is clean before use, it is necessary for the user to intentionally open the nozzle lid and directly confirm using the naked eye, which is troublesome. That is, it is a practical problem that the direct confirmation by the user before use is difficult. Therefore, even if the nozzle container is made clean by the ultraviolet light, the user may have misgivings that the nozzle container is dirty.

Thus, no matter how clean the private part wash nozzle is, if there are misgivings that the nozzle container is dirty due to the perception that the private part wash nozzle is stored in a dirty location, it is psychologically difficult to perceive that the private part wash nozzle is clean. As a result, there is a risk that a highly cleanliness-conscious user may no longer use the private part wash nozzle.

To solve such problems, it may be considered to leak a part of the ultraviolet light outside the nozzle container so that the user perceives that the nozzle container is being sterilized by the ultraviolet light. However, problems exist in that the user cannot visually confirm ultraviolet light; and as described above, the light cannot be leaked externally easily because the nozzle lid is provided at the opening of the nozzle container.

SUMMARY

According to the embodiment, a sanitary washing device includes a private part wash nozzle, a drive device, a casing, a nozzle lid, and an illuminator. The drive device causes the private part wash nozzle to advance and retract. The private part wash nozzle has a water discharge port dispensing washing water toward a private part of a user. The casing includes a nozzle container configured to store an entirety of the private part wash nozzle in a state in which the private part wash nozzle is retracted. The nozzle lid is provided to be openable and closable with respect to an opening provided at a front end of the nozzle container. The nozzle lid is in an open state in which the opening is open when the private part wash nozzle is advanced. The nozzle lid is in a closed state in which the opening is closed when the entirety of the private part wash nozzle is stored in the nozzle container. The illuminator irradiates sterilizing light having a sterilizing effect into an interior of the nozzle container. At least one of the nozzle lid or a vicinity of the nozzle lid is luminous in a state of being visible to the user when the nozzle lid is in the closed state and the sterilizing light from the illuminator is irradiated into the interior of the nozzle container.

BRIEF DESCRIPTION OF THE DRAWINGS

FIG. 4 is a plan view illustrating the internal structure of the sanitary washing device according to the embodiment;

DETAILED DESCRIPTION

Figure 1:
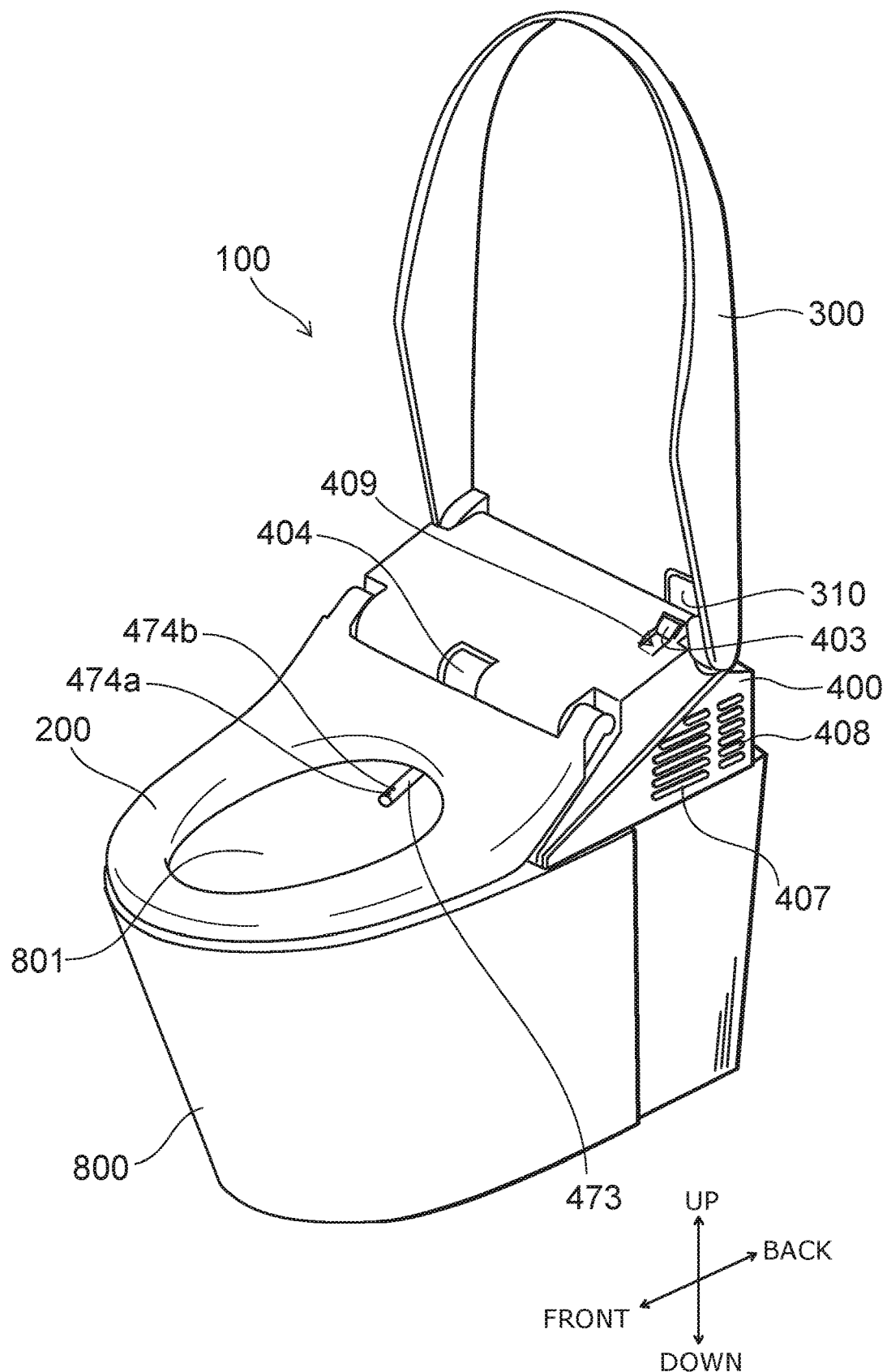
FIG. 1 is a perspective view illustrating a toilet device including a sanitary washing device according to an embodiment.

A first invention is a sanitary washing device, comprising a private part wash nozzle, a drive device causing the private part wash nozzle to advance and retract, a casing, a nozzle lid, and an illuminator; the private part wash nozzle has a water discharge port dispensing washing water toward a private part of a user; the casing includes a nozzle container configured to store an entirety of the private part wash nozzle in a state in which the private part wash nozzle is retracted; the nozzle lid is provided to be openable and closable with respect to an opening provided at a front end of the nozzle container; the nozzle lid is in an open state in which the opening is open when the private part wash nozzle is advanced; the nozzle lid is in a closed state in which the opening is closed when the entirety of the private part wash nozzle is stored in the nozzle container; the illuminator irradiates sterilizing light having a sterilizing effect into an interior of the nozzle container; and at least one of the nozzle lid or a vicinity of the nozzle lid is luminous in a state of being visible to the user when the nozzle lid is in the closed state and the sterilizing light from the illuminator is irradiated into the interior of the nozzle container.

According to the sanitary washing device, the penetration of urine or the like into the nozzle container can be suppressed because the opening of the nozzle container is closed by the nozzle lid when the entire private part wash nozzle is stored inside the nozzle container. The at least one of the nozzle lid or the vicinity of the nozzle lid is luminous in the state of being visible to the user when the nozzle lid is in the closed state and the sterilizing light is irradiated into the interior of the nozzle container from the illuminator; thereby, the user can visually be given a real sense that the interior of the nozzle container is being sterilized by the sterilizing light even when the nozzle lid is in the closed state. Thereby, the user can perceive that the private part wash nozzle is stored in a clean location; therefore, even a highly cleanliness-conscious user can use the private part wash nozzle with peace of mind.

A second invention is the sanitary washing device of the first invention, wherein the at least one of the nozzle lid or the vicinity of the nozzle lid is luminous by utilizing the sterilizing light irradiated into the interior of the nozzle container from the illuminator.

According to the sanitary washing device, the at least one of the nozzle lid or the vicinity of the nozzle lid is luminous by utilizing the sterilizing light irradiated into the interior of the nozzle container from the illuminator; thereby, the user can visually get an even realer sense that the interior of the nozzle container is sterilized by the sterilizing light.

A third invention is the sanitary washing device of the first or second invention, wherein the illuminator is provided in an interior of the casing and irradiates the sterilizing light including an ultraviolet light component.

According to the sanitary washing device, the sterilizing light that includes the ultraviolet light component is irradiated from the illuminator provided in the interior of the casing; thereby, the sterilizing light that includes the ultraviolet light component can be irradiated more reliably into the interior of the nozzle container.

A fourth invention is the sanitary washing device of the third invention, wherein the nozzle lid includes a wavelength conversion material configured to convert the ultraviolet light component into a visible light component; and the illuminator causes the nozzle lid to be luminous by the ultraviolet light component being converted into the visible light component at the nozzle lid.

According to the sanitary washing device, because the nozzle lid includes the wavelength conversion material, the nozzle lid that is positioned outside the nozzle container can be caused to be luminous even when a large clearance for leaking the light is not provided between the nozzle lid and the opening of the nozzle container. Thereby, the user can visually be given a real sense that the interior of the nozzle container is being sterilized by the sterilizing light while more reliably suppressing the penetration of the urine or the like between the nozzle lid and the opening of the nozzle container.

A fifth invention is the sanitary washing device of the third or fourth invention, wherein the illuminator irradiates the sterilizing light including the ultraviolet light component and a visible light component.

According to the sanitary washing device, the sterilizing light that includes the ultraviolet light component and the visible light component is irradiated from the illuminator provided in the interior of the casing; thereby, the user can perceive that the nozzle container is being sterilized by the sterilizing light even when another illuminator irradiating light including a visible light component or the like is not provided.

A sixth invention is the sanitary washing device of the fifth invention, wherein the nozzle lid includes a transmissive portion configured to transmit the visible light component; and the illuminator causes the nozzle lid to be luminous by causing the visible light component to pass through the transmissive portion.

According to the sanitary washing device, because the nozzle lid includes the transmissive portion, the visual confirmation effect by the user can be increased by the visible light component included in the sterilizing light irradiated from the illuminator passing through the transmissive portion while increasing the performance of sterilizing the interior of the nozzle container by the ultraviolet light component included in the sterilizing light irradiated from the illuminator.

A seventh invention is the sanitary washing device of the third or fourth invention that further comprises an other illuminator irradiating light including a visible light component; and the other illuminator irradiates the light including the visible light component on the at least one of the nozzle lid or the vicinity of the nozzle lid when the nozzle lid is in the closed state and the sterilizing light from the illuminator is irradiated into the interior of the nozzle container.

According to the sanitary washing device, the other illuminator that irradiates the light including the visible light component is provided in addition to the illuminator irradiating the sterilizing light including the ultraviolet light component; and the light that includes the visible light component is irradiated from the other illuminator on the at least one of the nozzle lid or the vicinity of the nozzle lid when irradiating the sterilizing light from the illuminator; thereby, the user can perceive that the nozzle container is being sterilized by the sterilizing light due to the light including the visible light component irradiated from the other illuminator even in the case where the sterilizing light irradiated from the illuminator does not include a visible light component.

An eighth invention is the sanitary washing device of the seventh invention, wherein the nozzle lid includes a transmissive portion configured to transmit the visible light component; and the other illuminator causes the nozzle lid to be luminous by causing the visible light component to pass through the transmissive portion.

According to the sanitary washing device, because the nozzle lid includes the transmissive portion, the visual confirmation effect by the user can be increased due to the visible light component included in the light irradiated from the other illuminator passing through the transmissive portion while increasing the performance of sterilizing the interior of the nozzle container by the ultraviolet light component included in the sterilizing light irradiated from the illuminator.

A ninth invention is the sanitary washing device of any one of the fifth to eighth inventions, wherein a radiant intensity of the ultraviolet light component is greater than a radiant intensity of the visible light component.

According to the sanitary washing device, the performance of sterilizing the interior of the nozzle container by the ultraviolet light component can be increased further by setting the radiant intensity of the ultraviolet light component to be greater than the radiant intensity of the visible light component.

A tenth invention is the sanitary washing device of any one of the first to ninth inventions, wherein a radiant intensity of the light from the at least one of the nozzle lid or the vicinity of the nozzle lid being caused to be luminous is less than a radiant intensity of the sterilizing light irradiated into the interior of the nozzle container from the illuminator.

According to the sanitary washing device, the irradiation of light having a strong sterilizing power on the user can be suppressed by setting the radiant intensity of the light from the at least one of the nozzle lid or the vicinity of the nozzle lid being caused to be luminous to be less than the radiant intensity of the sterilizing light irradiated into the interior of the nozzle container from the illuminator. Thereby, the performance of sterilizing the interior of the nozzle container can be increased while increasing the safety of the user.

An eleventh invention is the sanitary washing device of any one of the first to tenth inventions, wherein a peak wavelength of the light from the at least one of the nozzle lid or the vicinity of the nozzle lid being caused to be luminous is longer than a peak wavelength of the sterilizing light irradiated into the interior of the nozzle container from the illuminator.

According to the sanitary washing device, the irradiation of light having a strong sterilizing power on the user can be suppressed by setting the peak wavelength of the light from the at least one of the nozzle lid or the vicinity of the nozzle lid being caused to be luminous to be longer than the peak wavelength of the sterilizing light irradiated into the interior of the nozzle container from the illuminator. Thereby, the performance of sterilizing the interior of the nozzle container can be increased while increasing the safety of the user.

A twelfth invention is the sanitary washing device of any one of the first to eleventh inventions, wherein the nozzle lid includes a phosphorescent material.

According to the sanitary washing device, because the nozzle lid includes the phosphorescent material, the interior of the nozzle container can appear to be sterilized by the sterilizing light even when the sterilizing light actually is not being irradiated into the interior of the nozzle container. Thereby, the user can visually and more safely be given a real sense that the interior of the nozzle container is being sterilized by the sterilizing light.

A thirteenth invention is the sanitary washing device of any one of the first to twelfth inventions, further comprising a human body detection sensor and a controller; the human body detection sensor detects the user at a vicinity of the sanitary washing device; the controller controls the illuminator based on detection information of the human body detection sensor; and from a state in which the human body detection sensor does not detect the user, the controller causes the illuminator to operate when the human body detection sensor detects the user.

According to the sanitary washing device, by causing the illuminator to operate at the timing of detecting the user approaching the sanitary washing device, the user can perceive that the nozzle container is being sterilized by the sterilizing light before the user is seated on the toilet seat. Thereby, because the private part wash nozzle can be perceived as being stored in a clean location, even a highly cleanliness-conscious user can use the private part wash nozzle with peace of mind.

A fourteenth invention is the sanitary washing device of the thirteenth invention, further comprising a toilet seat where the user can contact the seat, and a seat contact detection sensor detecting the seat contact of the user on the toilet seat; and from a state in which the seat contact detection sensor does not detect the seat contact, the controller stops the operation of the illuminator when the seat contact detection sensor detects the seat contact.

According to the sanitary washing device, because the operation of the illuminator is stopped at the timing of the user being seated on the toilet seat, the irradiation of the sterilizing light on the user can be suppressed without losing the effect of the user perceiving that the nozzle container is being sterilized by the sterilizing light; and the safety of the user can be increased further.

A fifteenth invention is the sanitary washing device of the fourteenth invention, wherein the controller operates the illuminator even in the state in which the human body detection sensor does not detect the user.

According to the sanitary washing device, the irradiation time of the sterilizing light can be lengthened by irradiating the sterilizing light even in the state in which the human body detection sensor does not detect the user. The sterilization effect due to the sterilizing light can be increased thereby. By lengthening the irradiation time of the sterilizing light, the decrease of the sterilization effect can be suppressed even in the case where sterilizing light having a relatively long peak wavelength is irradiated. Accordingly, the safety of the user can be increased while suppressing the decrease of the sterilization effect. By irradiating the sterilizing light having the relatively long peak wavelength, the degradation of the resin members in the interior of the nozzle container also can be suppressed.

A sixteenth invention is the sanitary washing device of the fifteenth invention, wherein the controller controls the illuminator to cause an operation time of the illuminator in the state in which the human body detection sensor does not detect the user to be longer than an operation time of the illuminator in the state in which the human body detection sensor detects the user.

According to the sanitary washing device, by lengthening the operation time of the illuminator (the irradiation time of the sterilizing light) in the state in which the human body detection sensor does not detect the user, the sterilization effect of the interior of the nozzle container can be increased further.

Embodiments of the invention will now be described with reference to the drawings. Similar components in the drawings are marked with the same reference numerals; and a detailed description is omitted as appropriate.

FIG. 1 is a perspective view illustrating a toilet device including a sanitary washing device according to an embodiment.

As illustrated in FIG. 1, the toilet device includes a sit-down flush toilet (for convenience of description hereinbelow, called simply the "toilet") 800 and a sanitary washing device 100 mounted on the sit-down flush toilet 800. The sanitary washing device 100 includes a casing 400, a toilet seat 200, and a toilet lid 300. The toilet seat 200 and the toilet lid 300 each are pivotally supported openably and closeably with respect to the casing 400.

A private part washing functional part that realizes the washing of a private part such as a "bottom" or the like of the user sitting on the toilet seat 200, etc., are built into the interior of the casing 400. Also, for example, a seat contact detection sensor 404 that detects the user being seated on the toilet seat 200 is provided in the casing 400. When the seat contact detection sensor 404 detects the user sitting on the toilet seat 200, a private part wash nozzle (for convenience of description hereinbelow, called simply the "nozzle") 473 can be caused to advance into a bowl 801 of the toilet 800 or retract from the interior of the bowl 801 when the user operates an operation part 500 such as, for example, a remote control, etc. (referring to FIG. 2). A state in which the nozzle 473 is advanced into the bowl 801 is illustrated in the sanitary washing device 100 illustrated in FIG. 1.

The nozzle 473 washes the human private part by dispensing water (washing water) toward the human private part. A bidet wash water discharge port 474a and a bottom wash water discharge port 474b are provided in the tip part of the nozzle 473. The nozzle 473 can wash a female private part of a woman sitting on the toilet seat 200 by squirting water from the bidet wash water discharge port 474a provided in the tip of the nozzle 473. Or, the nozzle 473 can wash the "bottom" of the user sitting on the toilet seat 200 by squirting water from the bottom wash water discharge port 474b provided in the tip of the nozzle 473. In this specification, "water" includes not only cold water but also hot water that is heated.

The wash modes of the "bottom" include, for example, a "bottom wash" and a "gentle wash" that gently washes using a water stream that is softer than that of the "bottom wash." For example, the nozzle 473 can perform the "bidet wash," the "bottom wash," and the "gentle wash."

Although the bidet wash water discharge port 474a is provided further toward the tip side of the nozzle 473 than is the bottom wash water discharge port 474b in the nozzle 473 illustrated in FIG. 1, the mounting positions of the bidet wash water discharge port 474a and the bottom wash water discharge port 474b are not limited thereto. The bidet wash water discharge port 474a may be provided further toward the back end side of the nozzle 473 than is the bottom wash water discharge port 474b. Although two water discharge ports are provided in the nozzle 473 illustrated in FIG. 1, three or more water discharge ports may be provided.

Figure 2:
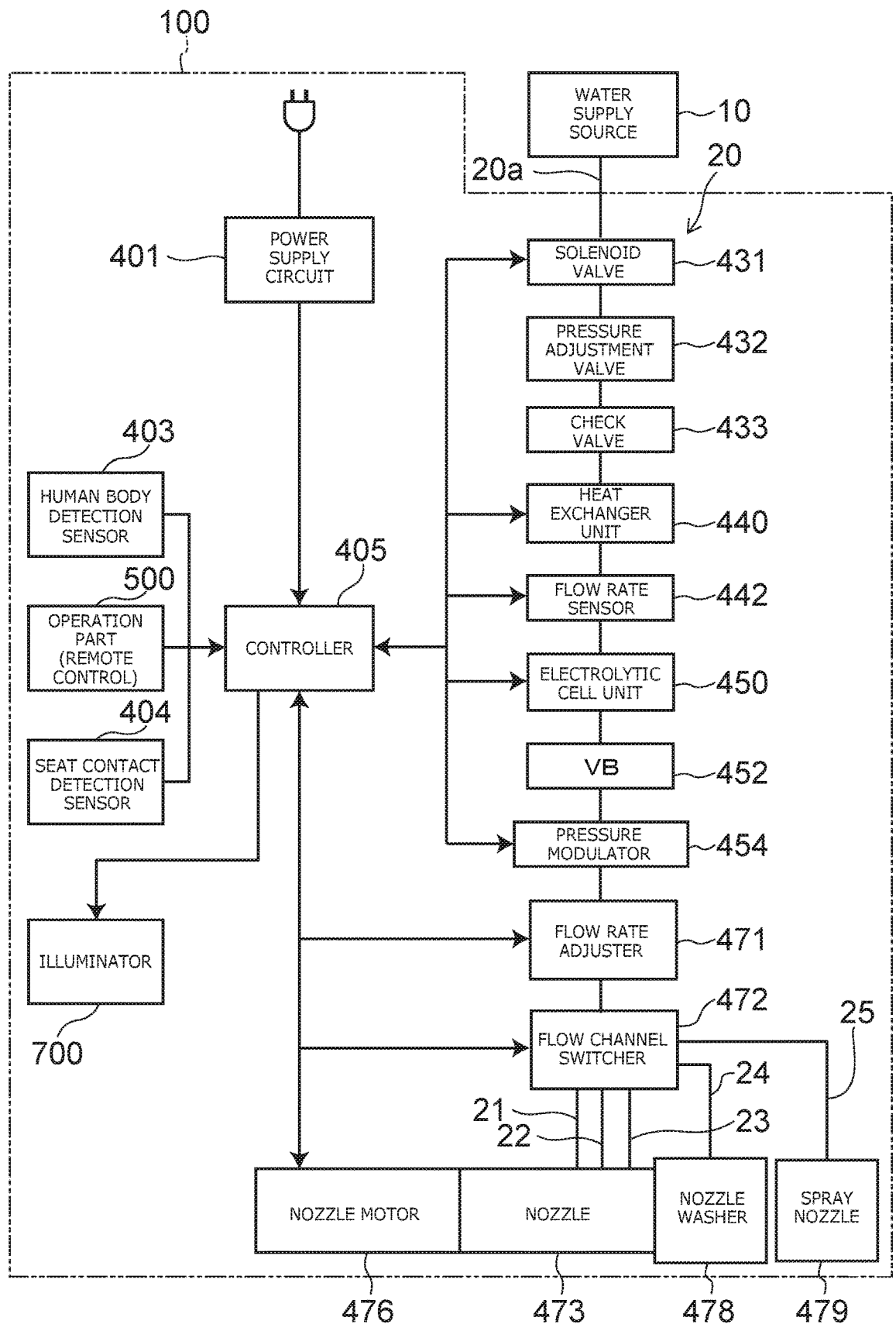
FIG. 2 is a block diagram illustrating the relevant components of the sanitary washing device according to the embodiment.

FIG. 2 is a block diagram illustrating the relevant components of the sanitary washing device according to the embodiment.

The relevant components of the water channel system and the electrical system are illustrated together in FIG. 2.

As illustrated in FIG. 2, the sanitary washing device 100 includes a conduit 20. The conduit 20 includes a pipe line 20a that reaches the nozzle 473 from a water supply source 10 such as a service water line, a water storage tank, etc. The conduit 20 guides the water supplied from the water supply source 10 to the nozzle 473 via the pipe line 20a. For example, the pipe line 20a is formed of components such as a solenoid valve 431, a heat exchanger unit 440, a flow channel switcher 472, etc., described below and multiple pipes that connect these components.

The solenoid valve 431 is provided at the upstream side of the conduit 20. The solenoid valve 431 is an openable and closable solenoid valve and controls the supply of the water based on a command from a controller 405 provided in the interior of the casing 400. In other words, the solenoid valve 431 opens and closes the pipe line 20a. The water that is supplied from the water supply source 10 flows in the pipe line 20a by setting the solenoid valve 431 to the open state.

The pressure adjustment valve 432 is provided downstream of the solenoid valve 431. The pressure adjustment valve 432 adjusts the pressure inside the pipe line 20a to be within a prescribed pressure range when the water supply pressure is high. A check valve 433 is provided downstream of the pressure adjustment valve 432. The check valve 433 suppresses the backward flow of water upstream of the check valve 433 when the pressure inside the pipe line 20a decreases, etc.

The heat exchanger unit 440 (the heater) is provided downstream of the check valve 433. The heat exchanger unit 440 includes a heater and heats the water supplied from the water supply source 10 to, for example, a specified temperature. In other words, the heat exchanger unit 440 produces warm water.

The heat exchanger unit 440 is, for example, an instantaneous-heating (instantaneous-type) heat exchanger that uses a ceramic heater, etc. Compared to a stored-hot-water heat exchanger that uses a hot water storage tank, the instantaneous-heating heat exchanger can heat the water to the specified temperature in a short period of time.

The heat exchanger unit 440 is not limited to the instantaneous-heating heat exchanger and may be a stored-hot-water heat exchanger. The heater is not limited to a heat exchanger; for example, another heating method that utilizes microwave heating, etc., may be used.

The heat exchanger unit 440 is connected to the controller 405. For example, the controller 405 heats the water to the temperature set by the operation part 500 by controlling the heat exchanger unit 440 according to an operation of the operation part 500 by the user.

A flow rate sensor 442 is provided downstream of the heat exchanger unit 440. The flow rate sensor 442 detects the flow rate of the water dispensed from the heat exchanger unit 440. In other words, the flow rate sensor 442 detects the flow rate of the water flowing through the pipe line 20a. The flow rate sensor 442 is connected to the controller 405. The flow rate sensor 442 inputs the detection result of the flow rate to the controller 405.

An electrolytic cell unit 450 is provided downstream of the flow rate sensor 442. The electrolytic cell unit 450 produces a liquid (functional water) including hypochlorous acid from the service water by electrolyzing the service water flowing through the interior of the electrolytic cell unit 450. The electrolytic cell unit 450 is connected to the controller 405. The electrolytic cell unit 450 produces the functional water based on a control by the controller 405.

The functional water that is produced by the electrolytic cell unit 450 may be, for example, a solution including metal ions such as silver ions, copper ions, etc. Or, the functional water that is produced by the electrolytic cell unit 450 may be a solution including electrolytic chlorine, ozone, etc. Or, the functional water that is produced by the electrolytic cell unit 450 may be acidic water or alkaline water.

A vacuum breaker (VB) 452 is provided downstream of the electrolytic cell unit 450. The vacuum breaker 452 includes, for example, a flow channel where the water flows, an intake port for intaking air into the flow channel, and a valve mechanism that opens and closes the intake port. For example, when water is flowing in the flow channel, the valve mechanism seals the intake port; and when the flow of the water stops, the valve mechanism intakes air into the flow channel by opening the intake port. In other words, the vacuum breaker 452 intakes air into the pipe line 20a when the water does not flow in the conduit 20. The valve mechanism includes, for example, a float valve.

For example, by intaking the air into the pipe line 20a as recited above, the vacuum breaker 452 promotes water drainage of the part of the pipe line 20a downstream of the vacuum breaker 452. For example, the vacuum breaker 452 promotes the water drainage of the nozzle 473. Thus, because the vacuum breaker 452 drains the water inside the nozzle 473 and intakes air into the nozzle 473, for example, the undesirable backward flow toward the water supply source 10 (the tap water) side of the washing water inside the nozzle 473, the liquid waste collected inside the bowl 801, etc., is suppressed.

A pressure modulator 454 is provided downstream of the vacuum breaker 452. The pressure modulator 454 applies a pulsatory motion or an acceleration to the flow of the water inside the pipe line 20a of the conduit 20 and applies a pulsatory motion to the water discharged from the bidet wash water discharge port 474a and the bottom wash water discharge port 474b of the nozzle 473 and/or the water discharger of a nozzle washer 478. In other words, the pressure modulator 454 causes the fluidic state of the water flowing through the pipe line 20a to fluctuate. The pressure modulator 454 is connected to the controller 405. The pressure modulator 454 causes the fluidic state of the water to fluctuate based on a control by the controller 405. The pressure modulator 454 causes the pressure of the water inside the pipe line 20a to fluctuate.

A flow rate adjuster 471 is provided downstream of the pressure modulator 454. The flow rate adjuster 471 adjusts the water force (the flow rate). The flow channel switcher 472 is provided downstream of the flow rate adjuster 471. The flow channel switcher 472 performs the opening and closing and/or the switching of the water supply to the nozzle 473 and/or the nozzle washer 478. The flow rate adjuster 471 and the flow channel switcher 472 may be provided as one unit. The flow rate adjuster 471 and the flow channel switcher 472 are connected to the controller 405. The operations of the flow rate adjuster 471 and the flow channel switcher 472 are controlled by the controller 405.

The nozzle 473, the nozzle washer 478, and a spray nozzle 479 are provided downstream of the flow channel switcher 472. The nozzle 473 receives a drive force from a nozzle motor 476, advances into the bowl 801 of the toilet 800, and retracts from the interior of the bowl 801. That is, the nozzle motor 476 is a drive device that causes the nozzle 473 to advance and retract based on a command from the controller 405.

For example, the nozzle washer 478 washes the outer perimeter surface (the central body) of the nozzle 473 by squirting water or functional water from a discharger. The spray nozzle 479 sprays the washing water or the functional water into the bowl 801 in a mist form. In the example, the spray nozzle 479 is provided separately from the nozzle 473 for washing the human body. This is not limited thereto; and a water discharge port for spraying a mist-like liquid into the bowl 801 may be provided in the nozzle 473.

A bottom wash flow channel 21, a gentle wash flow channel 22, and a bidet wash flow channel 23 also are provided downstream of the flow channel switcher 472. The bottom wash flow channel 21 and the gentle wash flow channel 22 guide, toward the bottom wash water discharge port 474b, the water supplied from the water supply source 10 or the functional water produced by the electrolytic cell unit 450 via the conduit 20. The bidet wash flow channel 23 guides, toward the bidet wash water discharge port 474a, the water supplied from the water supply source 10 or the functional water produced by the electrolytic cell unit 450 via the conduit 20.

A surface wash flow channel 24 and a spray flow channel 25 also are provided downstream of the flow channel switcher 472. The surface wash flow channel 24 guides, toward the water discharger of the nozzle washer 478, the water supplied from the water supply source 10 or the functional water produced by the electrolytic cell unit 450 via the conduit 20. The spray flow channel 25 guides, toward the spray nozzle 479, the water supplied from the water supply source 10 or the functional water produced by the electrolytic cell unit 450 via the conduit 20.

By controlling the flow channel switcher 472, the controller 405 switches the opening and closing of the flow channels of the bottom wash flow channel 21, the gentle wash flow channel 22, the bidet wash flow channel 23, the surface wash flow channel 24, and the spray flow channel 25. Thus, the flow channel switcher 472 switches between the state of communicating with the pipe line 20a and the state of not communicating with the pipe line 20a for each of the multiple water discharge ports of the bidet wash water discharge port 474a, the bottom wash water discharge port 474b, the nozzle washer 478, the spray nozzle 479, etc.

Electrical power is supplied to the controller 405 from a power supply circuit 401; and the controller 405 controls the operations of the solenoid valve 431, the heat exchanger unit 440, the electrolytic cell unit 450, the pressure modulator 454, the flow rate adjuster 471, the flow channel switcher 472, the nozzle motor 476, etc., based on signals from a human body detection sensor 403, the seat contact detection sensor 404, the flow rate sensor 442, the operation part 500, etc.

For example, the controller 405 also controls an illuminator 700 based on detection information of the human body detection sensor 403 and/or the seat contact detection sensor 404. The illuminator 700 irradiates, onto the periphery of the nozzle 473 (the nozzle container described below, etc.), sterilizing light which is light having a sterilizing effect. The illuminator 700 is described below.

As illustrated in FIG. 1, the human body detection sensor 403 is provided to be sunk into a recessed part 409 formed in the upper surface of the casing 400 and detects the user (the human body) approaching the toilet seat 200. In other words, the human body detection sensor 403 detects the user at the vicinity of the sanitary washing device 100. A transmissive window 310 is provided in the back part of the toilet lid 300. Therefore, the human body detection sensor 403 can detect the existence of the user via the transmissive window 310 in the state in which the toilet lid 300 is closed. For example, the controller 405 responds to the detection of the user by the human body detection sensor 403 by automatically opening the toilet lid 300.

Also, various mechanisms such as a "warm air drying function" that dries the "bottom" or the like of the user sitting on the toilet seat 200 by blowing warm air toward the "bottom" or the like, a "deodorizing unit," a "room heating unit," etc., may be provided as appropriate in the casing 400. In such a case, an exhaust port 407 from the deodorizing unit and an outlet 408 from the room heating unit are provided as appropriate in the side surface of the casing 400. However, in the invention, the sanitary washing functional parts and/or the other additional functional parts may not always be provided.

Figure 3A:
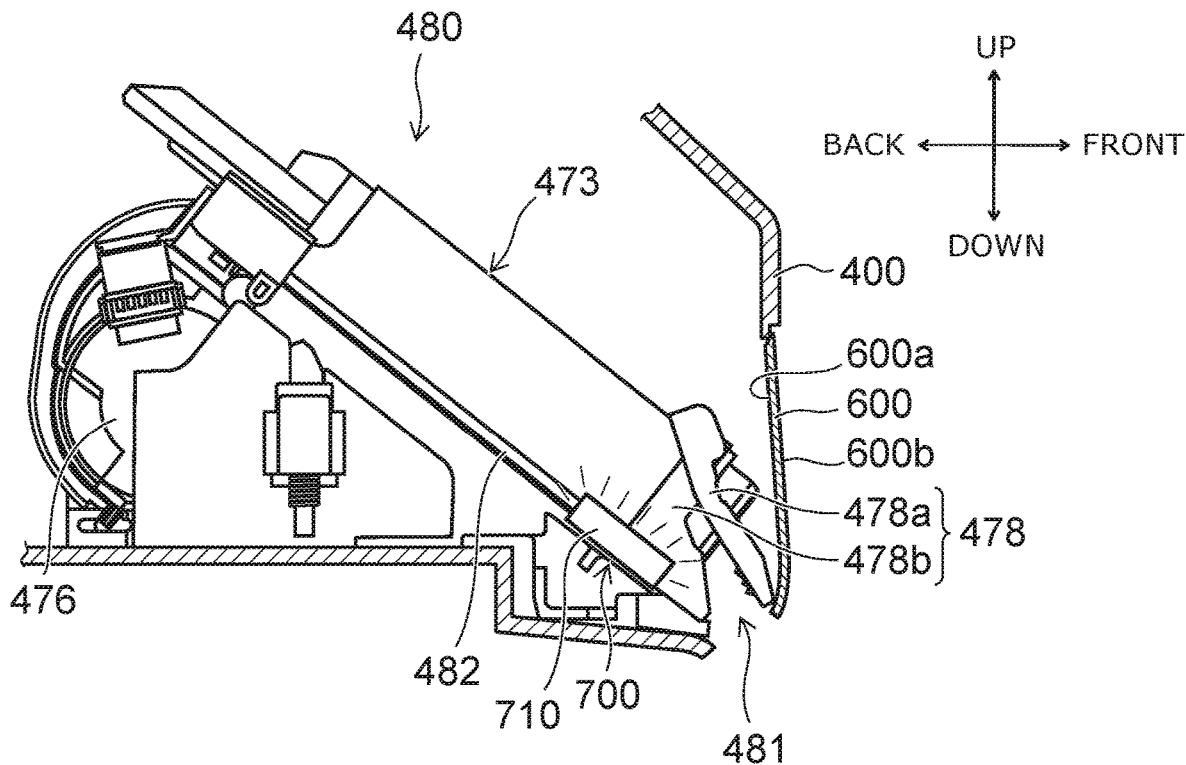
FIG. 3A and FIG. 3B are cross-sectional views illustrating the private part wash nozzle periphery of the sanitary washing device according to the embodiment.
Figure 3B:
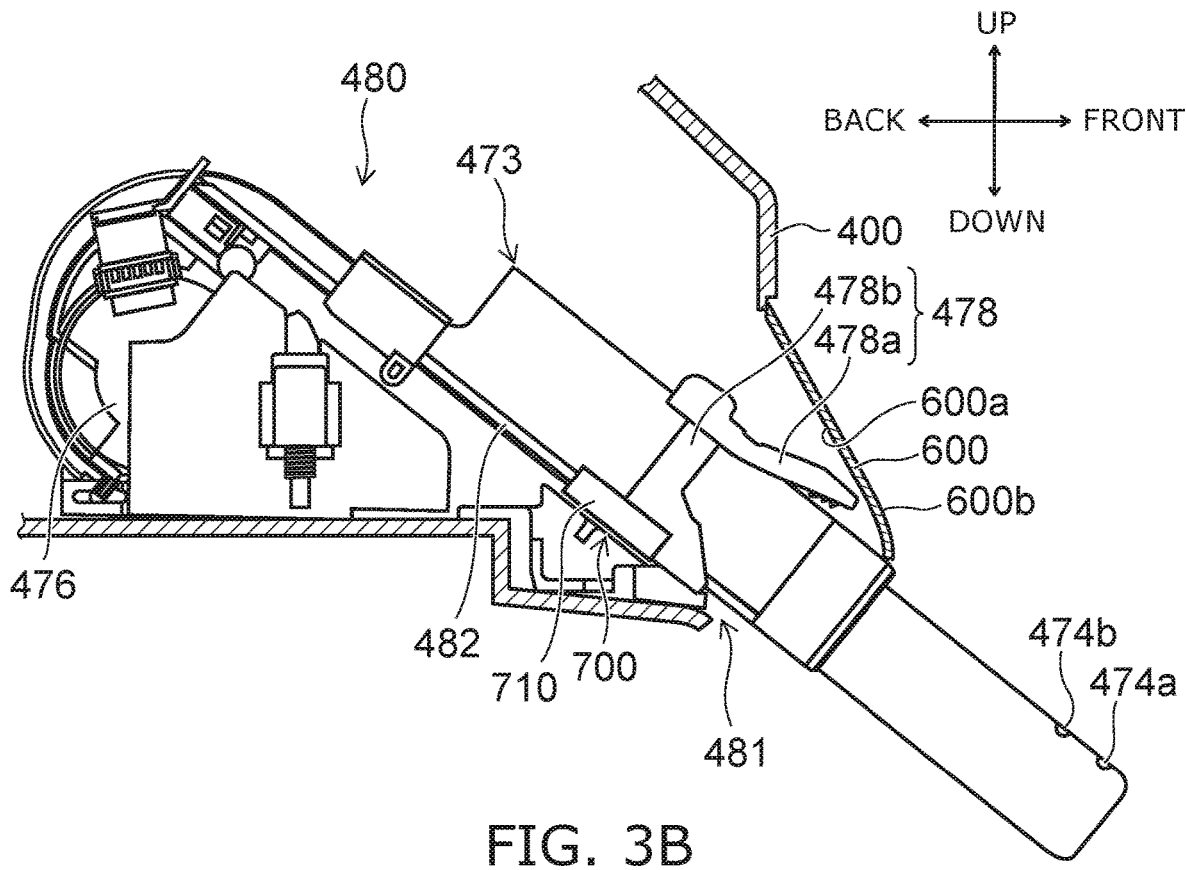

FIG. 3A and FIG. 3B are cross-sectional views illustrating the private part wash nozzle periphery of the sanitary washing device according to the embodiment.

FIG. 4 is a plan view illustrating the internal structure of the sanitary washing device according to the embodiment.

Figure 5:
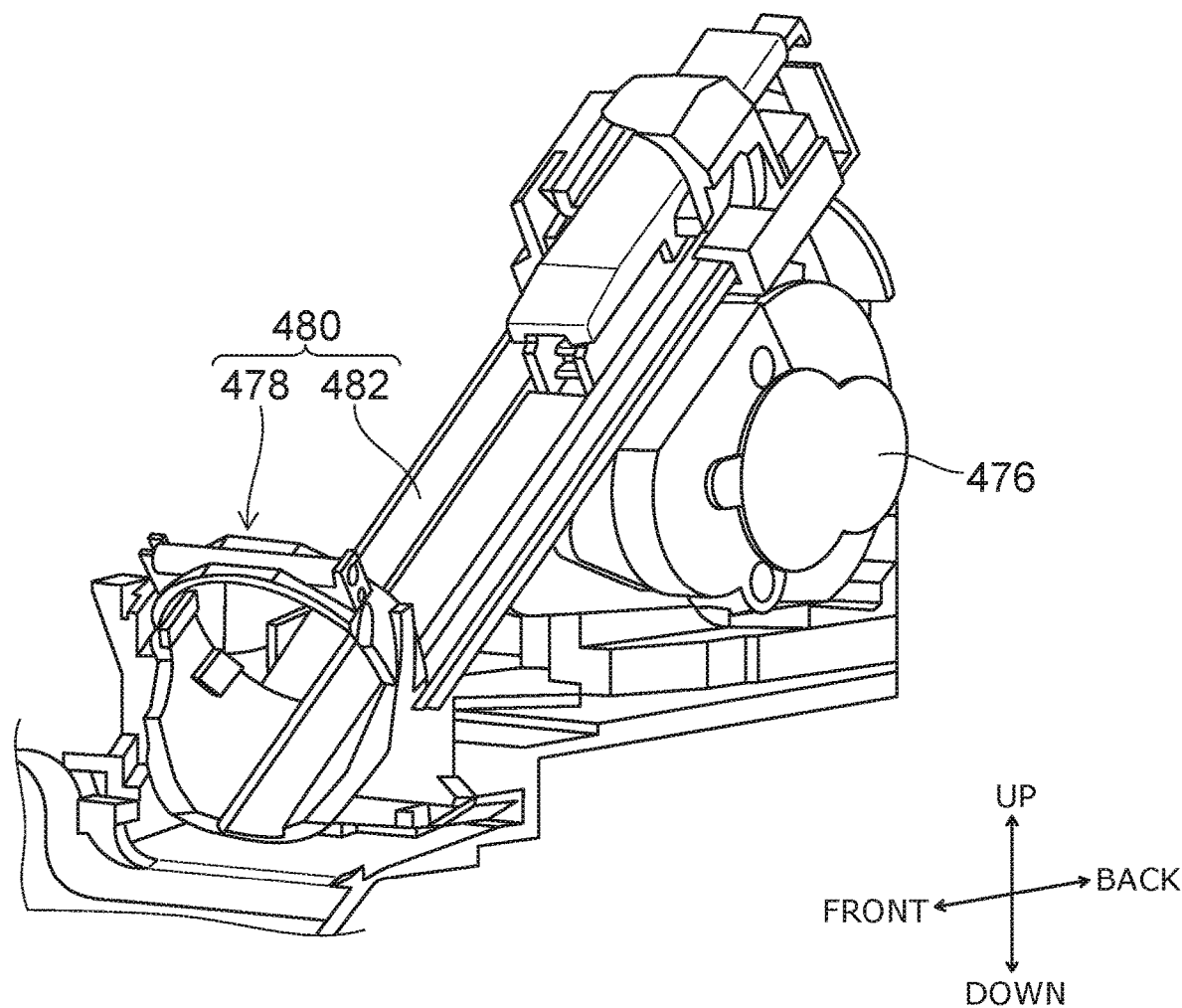
FIG. 5 is a perspective view illustrating the nozzle container of the sanitary washing device according to the embodiment.

FIG. 5 is a perspective view illustrating the nozzle container of the sanitary washing device according to the embodiment.

Figure 6:
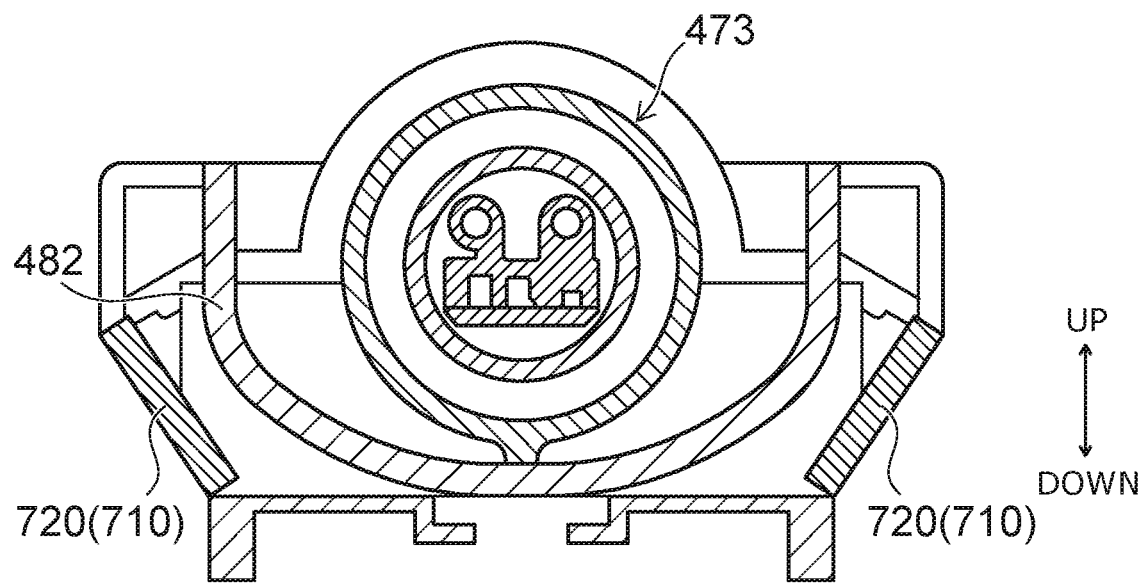
FIG. 6 is a front cross-sectional view illustrating the private part wash nozzle periphery of the sanitary washing device according to the embodiment.

FIG. 6 is a front cross-sectional view illustrating the private part wash nozzle periphery of the sanitary washing device according to the embodiment.

Figure 7:
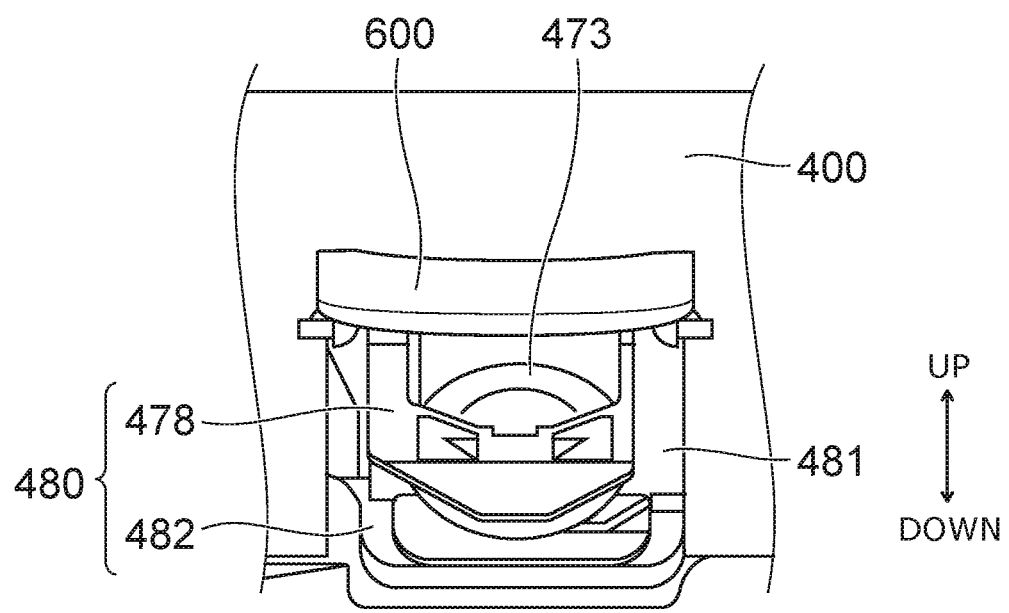
FIG. 7 is a front view illustrating the private part wash nozzle periphery of the sanitary washing device according to the embodiment.

FIG. 7 is a front view illustrating the private part wash nozzle periphery of the sanitary washing device according to the embodiment.

The configuration other than the nozzle 473 of the sanitary washing device 100 is not illustrated in FIG. 4.

As illustrated in FIG. 3A and FIG. 4, the casing 400 includes a nozzle container 480 that can store the entire nozzle 473 in the state in which the nozzle 473 is retracted. The nozzle container 480 is a member for storing the nozzle 473 and is adjacent to the nozzle 473 in the state in which the entire nozzle 473 is stored. In the example as illustrated in FIG. 5, a nozzle supporter 482 and the nozzle washer 478 are provided as the nozzle container 480.

The nozzle supporter 482 supports the nozzle 473 below the nozzle 473. The nozzle supporter 482 is tilted downward from the back toward the front. The nozzle 473 advances and retracts while sliding with respect to the nozzle supporter 482. For example, a tubular member that stores the nozzle 473 may be provided in the nozzle container 480.

The nozzle washer 478 is mounted to the front end of the nozzle supporter 482. As illustrated in FIG. 3A and FIG. 3B, the nozzle washer 478 includes a member (a water discharger) 478a in which water discharge holes discharging the washing water are formed, and a support body 478b of the member (the water discharger) 478a. As illustrated in FIG. 3A, FIG. 3B, and FIG. 7, an opening 481 is provided at the front end of the nozzle container 480. The opening 481 is provided at the lower part of the front end of the casing 400. The nozzle washer 478 is positioned backward of the opening 481. For example, the nozzle washer 478 washes the outer perimeter surface (the central body) of the nozzle 473 (self-cleaning) by squirting functional water or water from the water discharger 478a when the nozzle 473 advance and retracts.

A nozzle lid 600 is provided at the front of the nozzle 473. The nozzle lid 600 is provided to be openable and closable with respect to the opening 481 provided at the front end of the nozzle container 480. As illustrated in FIG. 3B, the nozzle lid 600 is in the open state in which the opening 481 is open when the nozzle 473 is advanced; and as illustrated in FIG. 3A, the nozzle lid 600 is in the closed state in which the opening 481 is closed when the entire nozzle 473 is stored in the nozzle container 480. For example, when the nozzle lid 600 is in the closed state, the front of the opening 481 is sealed with the nozzle lid 600.

The nozzle lid 600 has a back surface 600a and a front surface 600b. The back surface 600a is the surface positioned on the nozzle 473 side in the closed state. The front surface 600b is the surface positioned on the side opposite to the back surface 600a. In other words, the back surface 600a is the surface positioned on the back side in the closed state; and the front surface 600b is the surface positioned on the front side in the closed state.

In the state in which the nozzle 473 is not used, the nozzle 473 is stored in the nozzle container 480 as illustrated in FIG. 3A. When the private part wash is performed by the nozzle 473, the nozzle 473 slides frontward and downward with respect to the nozzle container 480. When the nozzle 473 slides frontward and downward, the nozzle 473 contacts the nozzle washer 478; and the nozzle lid 600 and the water discharger 478a of the nozzle washer 478 are pushed upward. For example, the nozzle 473 is washed by discharging water from the water discharger 478a until the nozzle 473 reaches a prescribed position.

When the nozzle 473 reaches the prescribed position as illustrated in FIG. 3B, water is discharged from the bidet wash water discharge port 474a or the bottom wash water discharge port 474b toward the private part of the user; and washing is performed. When the private part wash is completed. The nozzle 473 slides backward and upward toward the nozzle container 480. For example, the nozzle 473 is washed until the nozzle 473 is stored in the nozzle container 480 by discharging water from the water discharger 478a. The nozzle 473 retracts to a prescribed position and is stored in the nozzle container 480 as in the state illustrated in FIG. 3A.

As illustrated in FIG. 3A, FIG. 3B, FIG. 4, and FIG. 6, the sanitary washing device 100 includes the illuminator 700 irradiating sterilizing light which is light having a sterilizing effect. For example, the illuminator 700 is provided in the interior of the casing 400. In the example as illustrated in FIG. 4 and FIG. 6, the illuminator 700 includes two light emitters 710. The two light emitters 710 are provided respectively at the side parts of the nozzle supporter 482 at the lower left and right. The two light emitters 710 irradiate the sterilizing light toward the nozzle supporter 482 and the nozzle 473 positioned above the region between the two light emitters 710. The two light emitters 710 each are provided at the front side (the opening 481 side) of the nozzle container 480 and irradiate the sterilizing light onto the front side of the nozzle container 480.

The illuminator 700 includes, for example, a light-emitting element 720 (a light-emitting body). For example, the light-emitting element 720 is an LED (Light Emitting Diode). The light-emitting element 720 is not limited to an LED and may be, for example, a LD (Laser Diode), an OLED (Organic Light Emitting Diode), etc. The light-emitting element 720 may be, for example, a cold cathode fluorescent tube or a hot cathode fluorescent tube. The wavelength of the sterilizing light radiated by the light-emitting element 720 is, for example, 250 nm to 480 nm. For example, the light-emitting element 720 is connected to the controller 405 via a substrate and is switched ON and switched OFF based on a control of the controller 405. The controller 405 controls the operation of the illuminator 700 by controlling the ON and OFF of the light-emitting element 720. The controller 405 also may control the radiant intensity of the light-emitting element 720 by, for example, adjusting the voltage applied to the light-emitting element 720. For example, the light-emitting element 720 is provided in each of the light emitters 710.

The illuminator 700 irradiates the sterilizing light onto the nozzle container 480. For example, the illuminator 700 irradiates the sterilizing light into the interior of the nozzle container 480. Thereby, the nozzle container 480 is sterilized by the sterilizing light. In the example, the illuminator 700 irradiates the sterilizing light also onto the back surface 600a of the nozzle lid 600 and the front surface 600b of the nozzle lid 600. Thereby, the back surface 600a of the nozzle lid 600 and the front surface 600b of the nozzle lid 600 also are sterilized by the sterilizing light.

For example, by the irradiation of the sterilizing light, the illuminator 700 causes the annihilation or the deactivation of at least a part of the bacteria adhered to the nozzle container 480, etc. Thereby, the illuminator 700 reduces the living bacteria adhered to the nozzle container 480, etc. Thus, the illuminator 700 sterilizes the nozzle container 480, etc., by the irradiation of the sterilizing light.

Figure 8:
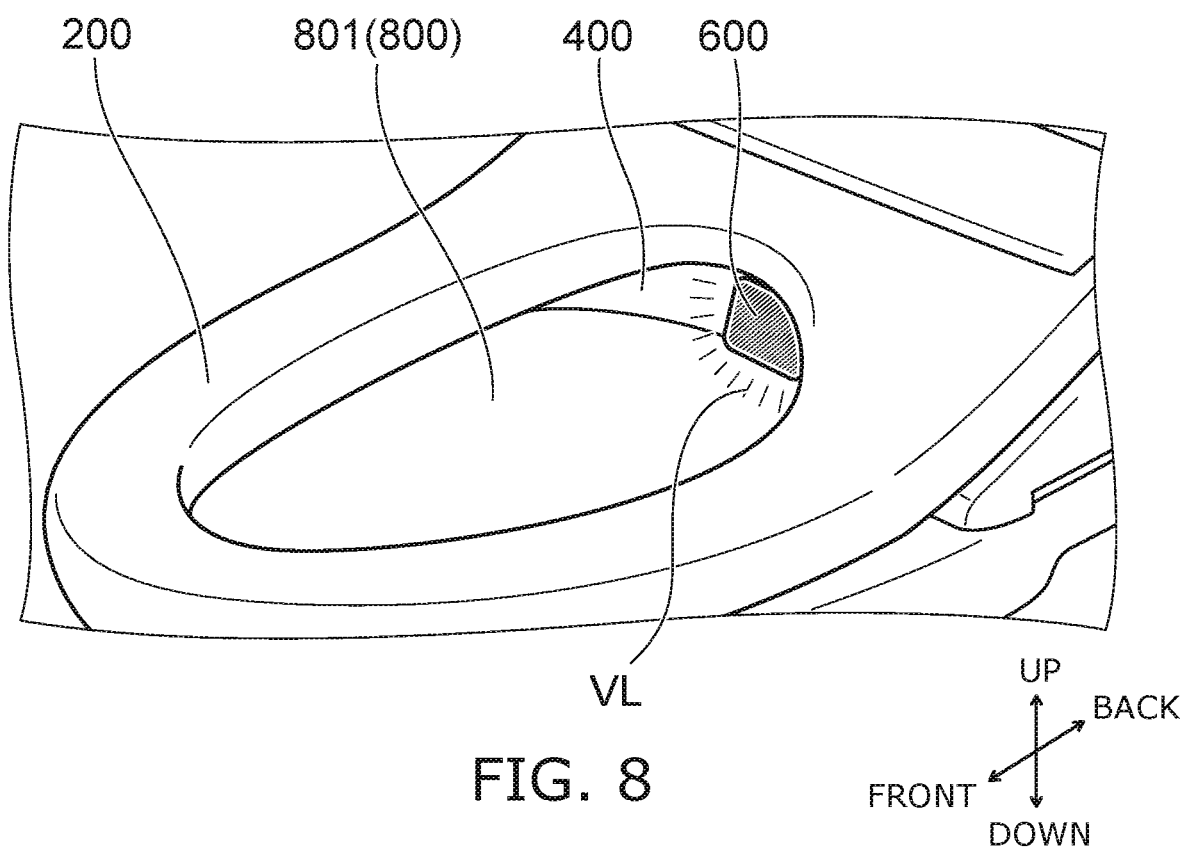
FIG. 8 is a perspective view illustrating the nozzle lid periphery of the sanitary washing device according to the embodiment.

FIG. 8 is a perspective view illustrating the nozzle lid periphery of the sanitary washing device according to the embodiment.

Figure 9:
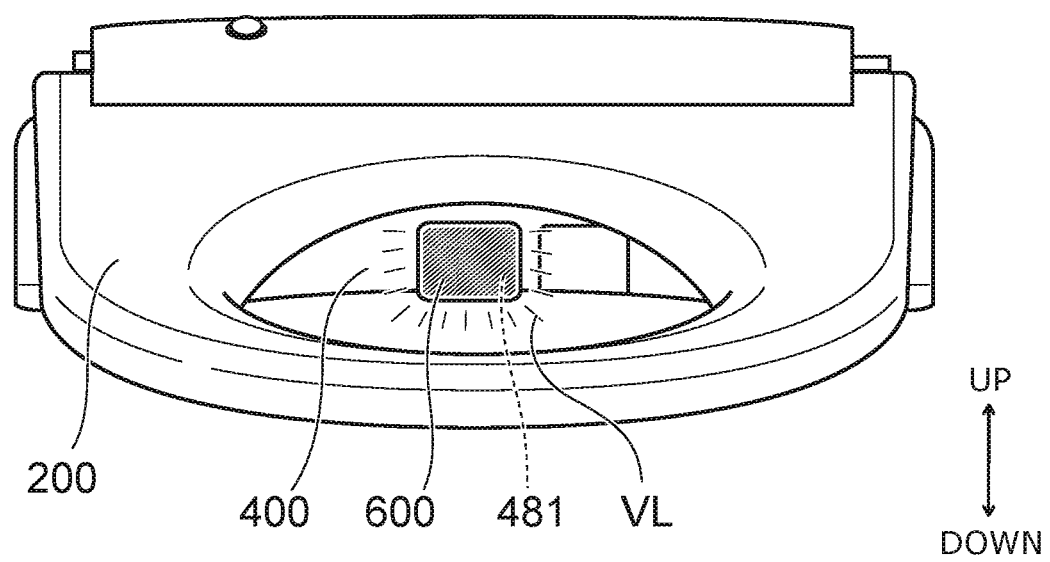
FIG. 9 is a front view illustrating the nozzle lid periphery of the sanitary washing device according to the embodiment.

FIG. 9 is a front view illustrating the nozzle lid periphery of the sanitary washing device according to the embodiment.

The toilet lid 300 is not illustrated in FIG. 9.

As illustrated in FIG. 8 and FIG. 9, when irradiating the sterilizing light when the nozzle lid 600 is in the closed state, the nozzle lid 600 and the illuminator 700 can emit visible light VL outside the casing 400 from the opening 481 or the nozzle lid 600. In the example, the nozzle lid 600 that can transmit the sterilizing light irradiated on the nozzle container 480 is provided; and the sterilizing light that is irradiated on the nozzle container 480 from the illuminator 700 passes through the nozzle lid 600 and is emitted outside the casing 400. In the example, the sterilizing light includes an ultraviolet light component and a visible light component.

For example, the irradiation of the sterilizing light is performed in the state in which the entire nozzle 473 is stored in the nozzle container 480 and the nozzle lid 600 is closed (i.e., the closed state of the nozzle lid 600). Accordingly, normally, the user does not easily perceive that the nozzle container 480 is being sterilized by the sterilizing light.

Conversely, in the embodiment, the visible light VL is emittable outside the casing 400 from the opening 481 or the nozzle lid 600; thereby, even in the state in which the nozzle lid 600 is provided at the opening 481 of the nozzle container 480, the user can perceive that the nozzle container 480 is being sterilized by the sterilizing light. Thereby, the nozzle 473 can be perceived as being stored in a clean location; therefore, even a highly cleanliness-conscious user can use the nozzle 473 with peace of mind.

Means in which the visible light VL is emittable outside the casing 400 from the opening 481 or the nozzle lid 600 when irradiating the sterilizing light when the nozzle lid 600 is in the closed state will now be described.

Figure 10:
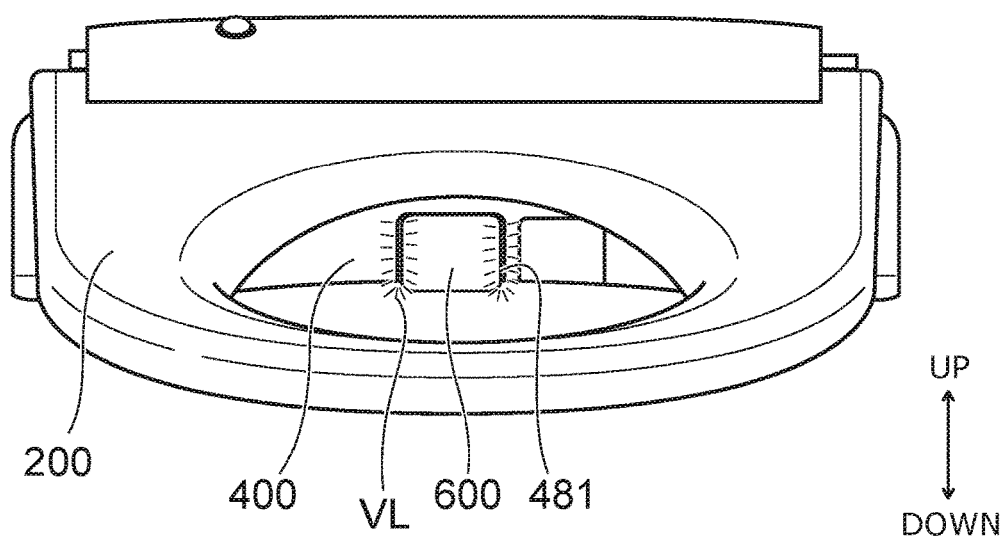
FIG. 10 is a front view illustrating a modification of the nozzle lid periphery of the sanitary washing device according to the embodiment.

FIG. 10 is a front view illustrating a modification of the nozzle lid periphery of the sanitary washing device according to the embodiment.

The toilet lid 300 is not illustrated in FIG. 10.

To emit the visible light VL outside the casing 400 from the opening 481 or the nozzle lid 600 when irradiating the sterilizing light when the nozzle lid 600 is in the closed state, it may be considered to emit (leak) the sterilizing light including the visible light component itself outside the casing 400 from the opening 481. More specifically, for example, as illustrated in FIG. 10, by providing a gap (clearance) between the nozzle lid 600 and the opening 481 of the nozzle container 480, the sterilizing light that is irradiated on the nozzle container 480 can be emitted outside the casing 400 from the gap between the opening 481 and the nozzle lid 600.

Thus, in the embodiment, by providing the gap (the clearance) between the nozzle lid 600 and the opening 481 of the nozzle container 480, the sterilizing light that is irradiated on the nozzle container 480 may be emitted outside the casing 400 from the gap between the opening 481 and the nozzle lid 600. In such a case, for example, the nozzle lid 600 may not transmit the sterilizing light.

Also, in the embodiment as recited above, the nozzle lid 600 that can transmit the sterilizing light irradiated on the nozzle container 480 may be provided. By providing the nozzle lid 600 that can transmit the sterilizing light, for example, the sterilizing light that is irradiated on the nozzle container 480 can pass through the nozzle lid 600 and can be emitted outside the casing 400 even when a large clearance is not provided between the nozzle lid 600 and the opening 481 of the nozzle container 480. Thereby, the user can be caused to perceive that the nozzle container 480 is being sterilized by the sterilizing light while suppressing the penetration of urine or the like into the nozzle container 480.

In the case where the sterilizing light does not include a visible light component, for example, the sterilizing light that does not include a visible light component may undergo wavelength conversion into light including a visible light component and may be emitted outside the casing 400 from the nozzle lid 600. More specifically, the nozzle lid 600 may include, for example, a wavelength conversion material. The wavelength conversion material is, for example, a material emitting light having a peak wavelength different from that of light irradiated on the wavelength conversion material (e.g., light having a peak wavelength longer than that of the irradiated light). The wavelength conversion material is, for example, a fluorescent material. The wavelength conversion material is, for example, 2,5-thiophenediyl-bis(5-tert-butyl-1,3-benzoxazole), etc.

Because the nozzle lid 600 includes the wavelength conversion material, the wavelength of the sterilizing light irradiated on the nozzle container 480 can be converted by the nozzle lid 600. Thereby, for example, because the light emitted outside the casing 400 from the nozzle lid 600 can have a longer wavelength than the sterilizing light, the user can be caused to perceive more safely that the nozzle container 480 is being sterilized by the sterilizing light.

For example, even in the case where the sterilizing light that has a small radiant intensity of the visible light component or does not include the visible light component is irradiated on the nozzle container 480, the sterilizing light can be converted into the light including the visible light component by the wavelength conversion material and emitted outside the casing 400. Thereby, the sterilization effect can be increased further by an ultraviolet light component having a high sterilizing performance; and the visual confirmation effect by the user also can be satisfied by emitting, outside the casing 400, the light converted to include the visible light component.

In the embodiment, the nozzle lid 600 may include, for example, a phosphorescent material. The phosphorescent material is, for example, a material that absorbs the energy of the irradiated light and emits the energy as light. The phosphorescent material is, for example, strontium aluminate, etc.

Because the sterilizing light is light that has a sterilizing effect, basically, it is favorable not to irradiate the sterilizing light on the user. Because the nozzle lid 600 includes the phosphorescent material, it can appear that the sterilizing light is sterilizing the interior of the nozzle container 480 even when the sterilizing light actually is not being irradiated into the interior of the nozzle container 480. Thereby, the user can be caused to perceive more safely that the interior of the nozzle container 480 is being sterilized by the sterilizing light.

The sterilizing light that is irradiated from the illuminator 700 will now be described.

In the embodiment, for example, the illuminator 700 irradiates the sterilizing light including the ultraviolet light component and the visible light component. Thus, by irradiating onto the nozzle container 480 the irradiated light including both the ultraviolet light component having the high sterilizing performance and the visible light component that is visible but has a lower sterilizing performance than the ultraviolet light component, for example, the sterilization effect due to the sterilizing light and the visual confirmation effect by the user both can be realized in the case where the sterilizing light itself is emitted (leaked) outside the casing 400 from the opening 481.

It is sufficient for the radiant intensity of the visible light component to be enough to be visible to the user; and it is desirable to increase the radiant intensity of the ultraviolet light component to increase the sterilization effect. Therefore, in the embodiment, for example, the illuminator 700 irradiates the sterilizing light in which the radiant intensity of the ultraviolet light component is greater than the radiant intensity of the visible light component. Thereby, the sterilization effect can be increased further while satisfying the visual confirmation effect by the user.

The peak wavelength of the sterilizing light is, for example, not less than 250 nm and not more than 480 nm. Favorably, the peak wavelength of the sterilizing light is not less than 350 nm and not more than 480 nm. Thus, by setting the peak wavelength of the sterilizing light to be near 400 nm (e.g., not less than 350 nm and not more than 480 nm) which is the boundary between the visible region and the ultraviolet region, the sterilizing light that includes the ultraviolet light component and the visible light component can be irradiated from one light source (the light-emitting element 720). Thereby, the number of light sources provided in the illuminator 700 can be reduced; and the sanitary washing device 100 can be downsized.

Figure 11:
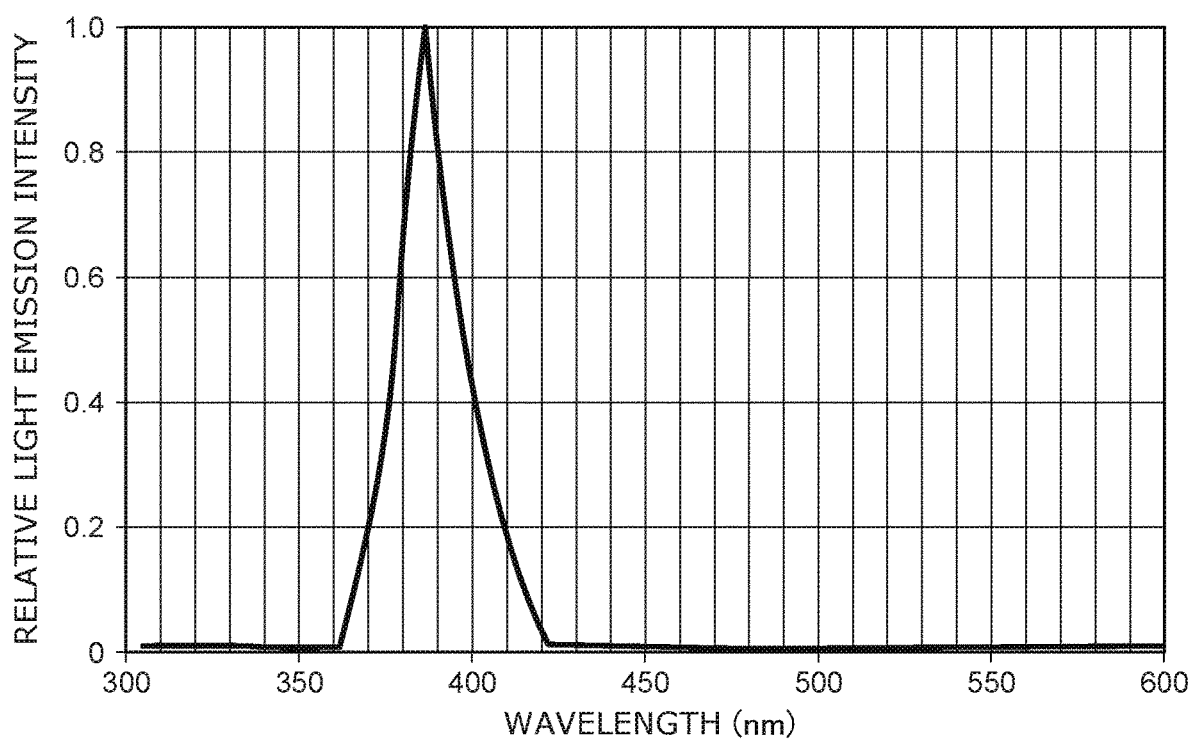
FIG. 11 is a graph illustrating an example of the wavelength distribution of the sterilizing light of the sanitary washing device according to the embodiment.

FIG. 11 is a graph illustrating an example of the wavelength distribution of the sterilizing light of the sanitary washing device according to the embodiment.

In the example as illustrated in FIG. 11, the sterilizing light includes light of a wavelength of about 360 nm to about 420 nm; and the peak wavelength is about 385 nm. Thus, by setting the peak wavelength of the sterilizing light at the boundary vicinity between the visible region and the ultraviolet region, for example, the sterilizing light that includes a UV-A component (not less than 315 nm and not more than 400 nm) which is the ultraviolet light component and a violet-to-blue visible light component (not less than 400 nm and not more than 480 nm) can be irradiated. Using such a sterilizing light, both the sterilization effect and the visual confirmation effect by the user can be realized.

The light source of the sterilizing light is not limited to one light source. For example, as the sterilizing light, light that includes an ultraviolet light component but does not include a visible light component may be irradiated from one light source, and light that includes a visible light component but does not include an ultraviolet light component may be irradiated from another light source. In other words, the ultraviolet light component and the visible light component included in the sterilizing light may be irradiated simultaneously from different light sources.

The sterilizing light is not limited to light including an ultraviolet light component and a visible light component. For example, in the case where the nozzle lid 600 includes the wavelength conversion material, the sterilizing light may be light that includes an ultraviolet light component but does not include a visible light component.

Figure 12:
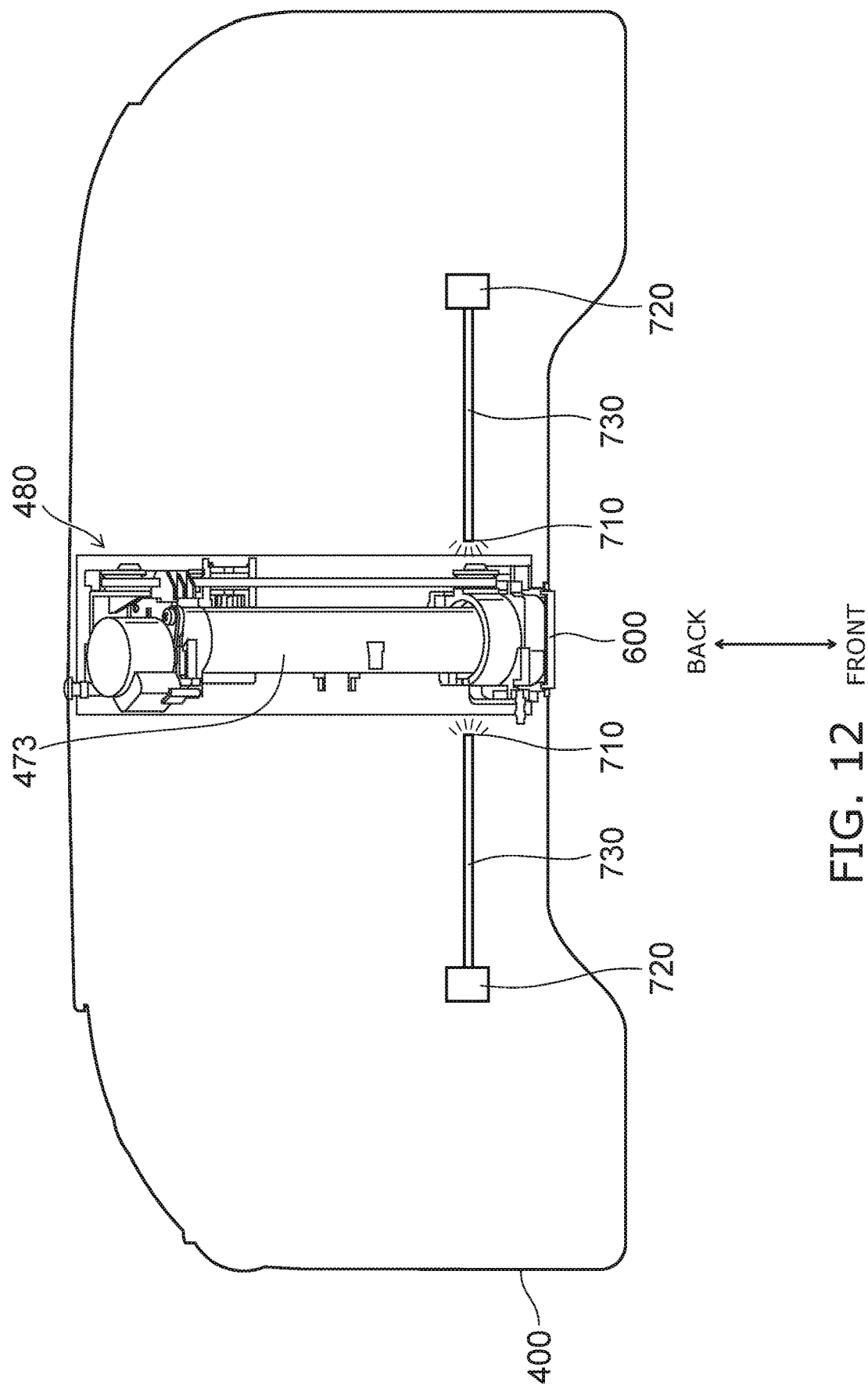
FIG. 12 is a plan view illustrating a modification of the illuminator of the sanitary washing device according to the embodiment.

FIG. 12 is a plan view illustrating a modification of the illuminator of the sanitary washing device according to the embodiment.

As illustrated in FIG. 12, the light-emitting element 720 may be provided at a position distal to the nozzle container 480. In the example, two light-emitting elements 720 are provided at positions distal to the nozzle container 480 at the left and right; and the two light-emitting elements 720 are connected via optical fibers 730 respectively to two light emitters 710 provided at the side parts of the nozzle container 480 on the left and right.

Thus, in the embodiment, the sterilizing light may be guided from the light-emitting element 720 to the light emitter 710 by the optical fiber 730 or the like; and the sterilizing light may be irradiated on the nozzle container 480 from the light emitter 710 provided at the nozzle container 480 vicinity.

A specific example of the operation of the sanitary washing device according to the embodiment will now be described with reference to the drawings.

Figure 13:
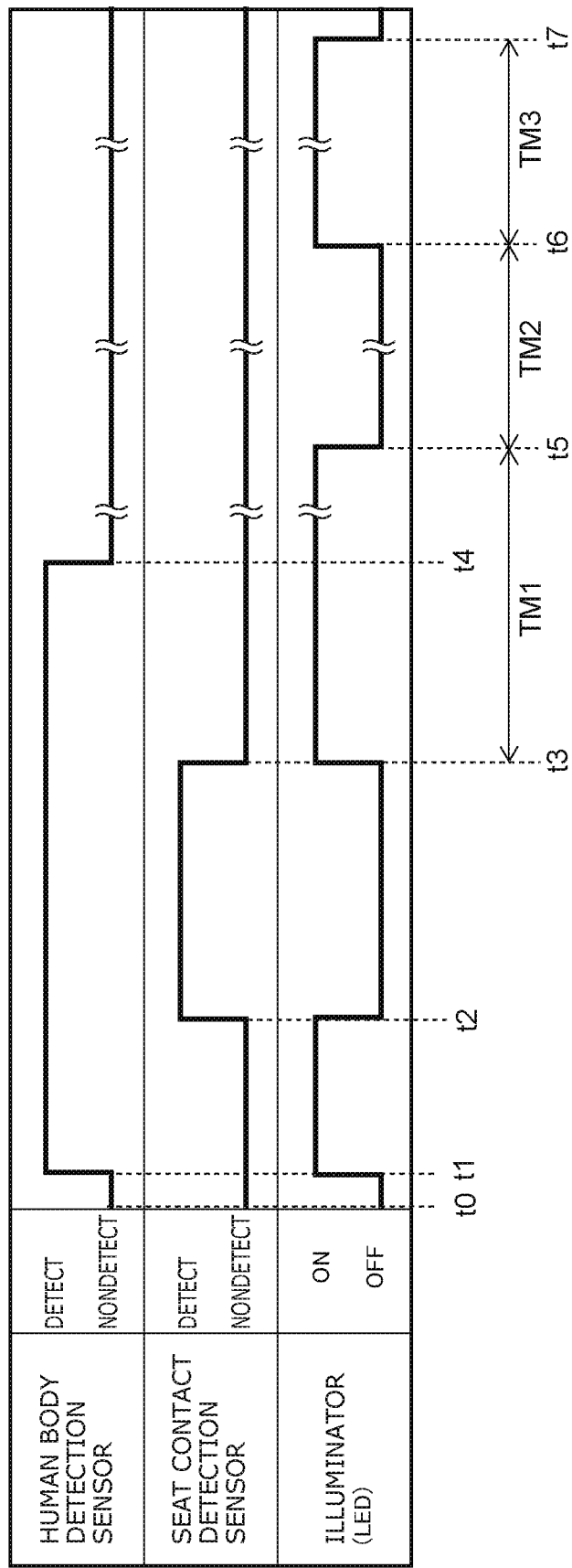
FIG. 13 is a timing chart illustrating a specific example of the operation of the sanitary washing device according to the embodiment.

FIG. 13 is a timing chart illustrating a specific example of the operation of the sanitary washing device according to the embodiment.

As illustrated in FIG. 13, the illuminator 700 does not operate in the state in which the human body detection sensor 403 does not detect the user (a timing t0). More specifically, the light-emitting element 720 of the illuminator 700 (e.g., the LED) is switched OFF (OFF).

When the human body detection sensor 403 detects the user approaching the sanitary washing device 100, the controller 405 operates the illuminator 700 (a timing t1). More specifically, the controller 405 switches ON the light-emitting element 720 of the illuminator 700 (ON). In the case where the illuminator 700 is being operated in a state in which the user is not detected, the controller 405 continues to operate the illuminator 700 even after the user is detected.

Thus, the user can be caused to perceive that the nozzle container 480 is being sterilized by the sterilizing light before the user is seated on the toilet seat 200 by operating the illuminator 700 at the timing of detecting the user approaching the sanitary washing device 100. Thereby, even a highly cleanliness-conscious user can use the nozzle 473 with peace of mind because the nozzle 473 can be perceived as being stored in a clean location.

For example, the illuminator 700 continues to operate until the seat contact detection sensor 404 detects the seat contact of the user. In other words, the controller 405 continues to operate the illuminator 700 in the state in which the human body detection sensor 403 has detected the user but the seat contact detection sensor 404 has not detected the seat contact.

When the seat contact detection sensor 404 detects the seat contact of the user, the controller 405 stops the operation of the illuminator 700 (a timing t2). More specifically, the controller 405 switches OFF the light-emitting element 720 of the illuminator 700 (OFF).

After the user is seated on the toilet seat 200, the user can no longer visually confirm the nozzle container 480. Also, in the case where the sterilizing light is caused to leak outside the casing 400 from the opening 481, a part of the sterilizing light easily may be irradiated on the user. Conversely, by stopping the operation of the illuminator 700 at the timing of the user being seated on the toilet seat 200, the irradiation of the sterilizing light on the user can be suppressed without losing the effect of the user perceiving that the nozzle container 480 is being sterilized by the sterilizing light; and the safety of the user can be increased further.

For example, the illuminator 700 continues to stop the operation until the seat contact detection sensor 404 detects the user rising from the seat. In other words, the controller 405 continues to stop the operation of the illuminator 700 in the state in which the seat contact detection sensor 404 detects the seat contact.

The controller 405 operates the illuminator 700 when the seat contact detection sensor 404 detects the user rising from the seat (the state changing from the state in which the seat contact detection sensor 404 detects the seat contact to the state in which the seat contact is not detected) (a timing t3). More specifically, the controller 405 switches ON the light-emitting element 720 of the illuminator 700 (ON). Thereby, the user that has risen from the seat can perceive that the sterilization of the nozzle container 480 has restarted.

The illuminator 700 continues to operate until a prescribed period of time TM1 has elapsed. In other words, even when the state in which the human body detection sensor 403 detects the user changes to the state in which the user is not detected, the controller 405 continues to operate the illuminator 700 until the prescribed period of time TM1 has elapsed (a timing t4).

When the prescribed period of time TM1 has elapsed, the controller 405 stops the operation of the illuminator 700 (a timing t5). More specifically, the controller 405 switches OFF the light-emitting element 720 of the illuminator 700 (OFF).

The illuminator 700 is operated when a prescribed period of time TM2 has elapsed in the unused state. In other words, the controller 405 operates the illuminator 700 when the prescribed period of time TM2 has elapsed in the state in which the human body detection sensor 403 does not detect the user and the seat contact detection sensor 404 does not detect the seat contact (a timing t6). More specifically, the controller 405 switches ON the light-emitting element 720 of the illuminator 700 (ON). Thus, the controller 405 may operate the illuminator 700 in the state in which the human body detection sensor 403 does not detect the user.

The irradiation time of the sterilizing light can be lengthened by irradiating the sterilizing light even in the state in which the human body detection sensor 403 does not detect the user. The sterilization effect due to the sterilizing light can be increased thereby. Even in the case where the sterilizing light having a relatively long peak wavelength is irradiated, the decrease of the sterilization effect can be suppressed by lengthening the irradiation time of the sterilizing light. Accordingly, the safety of the user can be increased while suppressing the decrease of the sterilization effect. Also, the degradation of the resin members in the interior of the nozzle container 480 also can be suppressed by irradiating the sterilizing light having the relatively long peak wavelength.

The controller 405 stops the operation of the illuminator 700 when a prescribed period of time TM3 has elapsed (a timing t7). More specifically, the controller 405 switches OFF the light-emitting element 720 of the illuminator 700 (OFF).

The prescribed periods of time TM1 to TM3 may be any time. For example, the prescribed periods of time TM1 to TM3 are set so that the operation time of the illuminator 700 in the state in which the human body detection sensor 403 does not detect the user is longer than the operation time of the illuminator 700 in the state in which the human body detection sensor 403 detects the user. In other words, for example, the controller 405 controls the illuminator 700 so that the operation time of the illuminator 700 in the state in which the human body detection sensor 403 does not detect the user is longer than the operation time of the illuminator 700 in the state in which the human body detection sensor 403 detects the user. Thus, by lengthening the operation time of the illuminator 700 (the irradiation time of the sterilizing light) in the state in which the human body detection sensor 403 does not detect the user, the sterilization effect of the interior of the nozzle container 480 can be increased further.

Figure 14:
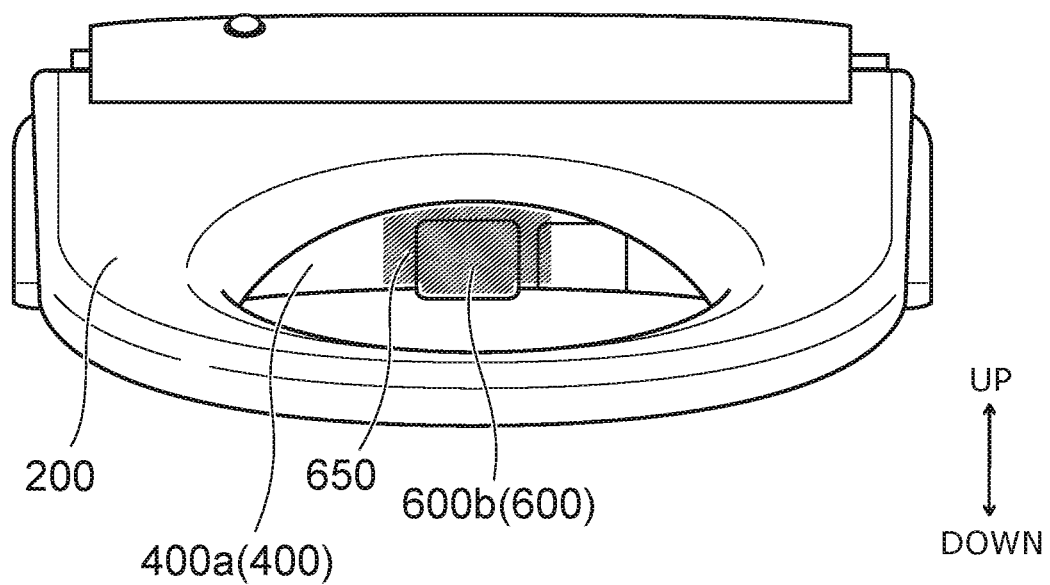
FIG. 14 is a front view illustrating the nozzle lid periphery of the sanitary washing device according to the embodiment.

FIG. 14 is a front view illustrating the nozzle lid periphery of the sanitary washing device according to the embodiment.

As illustrated in FIG. 14, at least one of the nozzle lid 600 or a vicinity 650 of the nozzle lid 600 is luminous in the state of being visible to the user when the sterilizing light from the illuminator 700 is irradiated into the interior of the nozzle container 480 when the nozzle lid 600 is in the closed state.

The nozzle lid 600 and the vicinity 650 of the nozzle lid 600 are shown by hatching in FIG. 14. That is, in the embodiment, at least a part of the region shown by the hatching in FIG. 14 is luminous in the state of being visible to the user when the sterilizing light from the illuminator 700 is irradiated into the interior of the nozzle container 480 when the nozzle lid 600 is in the closed state. At least the front surface 600b (the outer surface) is luminous in the case where the nozzle lid 600 is luminous. At least the surface (the outer surface) on the front surface 600b side of the nozzle lid 600 is luminous in the case where the vicinity 650 of the nozzle lid 600 is luminous.

The vicinity 650 of the nozzle lid 600 includes, for example, a part of a front surface 400a of the casing 400 and the gap (the clearance) between the nozzle lid 600 and the opening 481 of the nozzle container 480. More specifically, the vicinity 650 of the nozzle lid 600 is, for example, the region within 5 cm of the nozzle lid 600.

In this specification, "luminous in the state of being visible to the user" is, for example, the state in which at least one of the nozzle lid 600 or the vicinity 650 of the nozzle lid 600 is brighter than the other parts (e.g., the part of the front surface 400a of the casing 400 not less than 5 cm away from the nozzle lid 600). The state of being "luminous in the state of being visible to the user" is not limited to the state in which at least one of the nozzle lid 600 or the vicinity 650 of the nozzle lid 600 emits visible light. The state of being "luminous in the state of being visible to the user" may be, for example, the state in which visible light irradiated from a light source passes through at least one of the nozzle lid 600 or the vicinity 650 of the nozzle lid 600 and the transmission location is brightly illuminated, or the state in which visible light irradiated from a light source is reflected by at least one of the nozzle lid 600 or the vicinity 650 of the nozzle lid 600 and the reflection location is brightly illuminated.

Thus, according to the embodiment, in the state in which the entire nozzle 473 is stored in the interior of the nozzle container 480, the opening 481 of the nozzle container 480 is closed by the nozzle lid 600; therefore, the penetration of urine or the like into the interior of the nozzle container 480 can be suppressed. Also, at least one of the nozzle lid 600 or the vicinity 650 of the nozzle lid 600 is luminous in the state of being visible to the user when the sterilizing light from the illuminator 700 is irradiated into the interior of the nozzle container 480 when the nozzle lid 600 is in the closed state; thereby, even in the state in which the nozzle lid 600 is closed, the user can visually be given a real sense that the interior of the nozzle container 480 is being sterilized by the sterilizing light. Thereby, the user can perceive that the nozzle 473 is stored in a clean location; therefore, even a highly cleanliness-conscious user can use the nozzle 473 with peace of mind.

For example, at least one of the nozzle lid 600 or the vicinity 650 of the nozzle lid 600 is caused to be luminous by utilizing the sterilizing light irradiated into the interior of the nozzle container 480 from the illuminator 700. In other words, for example, the illuminator 700 causes at least one of the nozzle lid 600 or the vicinity 650 of the nozzle lid 600 to be luminous by utilizing the sterilizing light irradiated into the interior of the nozzle container 480.

Thus, by causing at least one of the nozzle lid 600 or the vicinity 650 of the nozzle lid 600 to be luminous by utilizing the sterilizing light irradiated into the interior of the nozzle container 480 from the illuminator 700, the user can visually get an even realer sense that the interior of the nozzle container 480 is being sterilized by the sterilizing light.

Figure 15A:
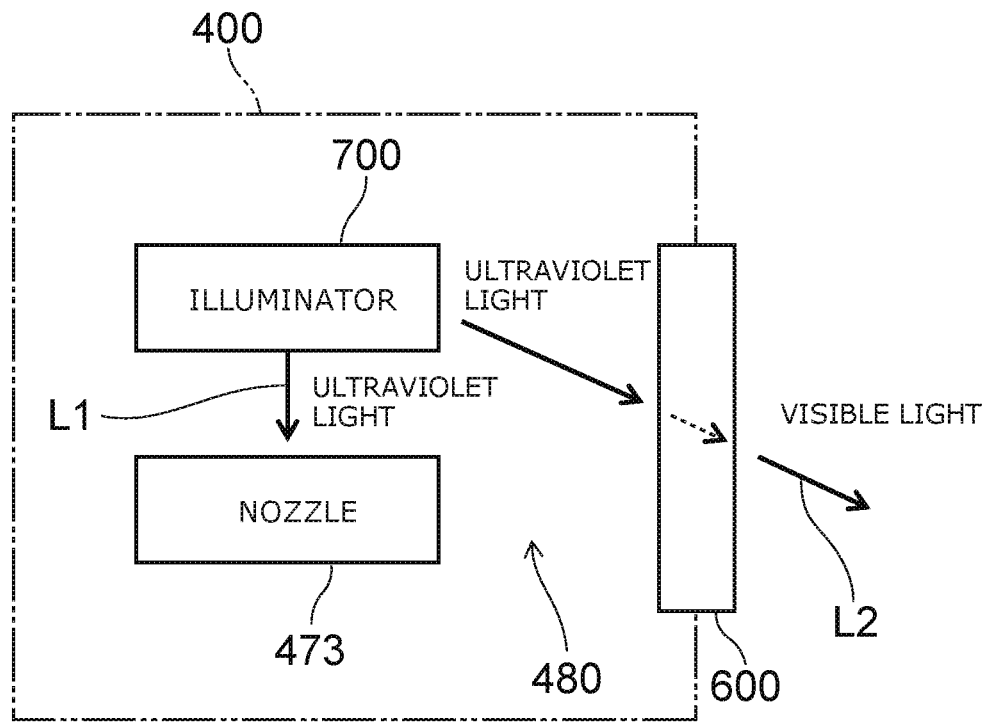
FIG. 15A and FIG. 15B are descriptive views schematically illustrating the illuminator periphery of the sanitary washing device according to the embodiment.
Figure 15B:
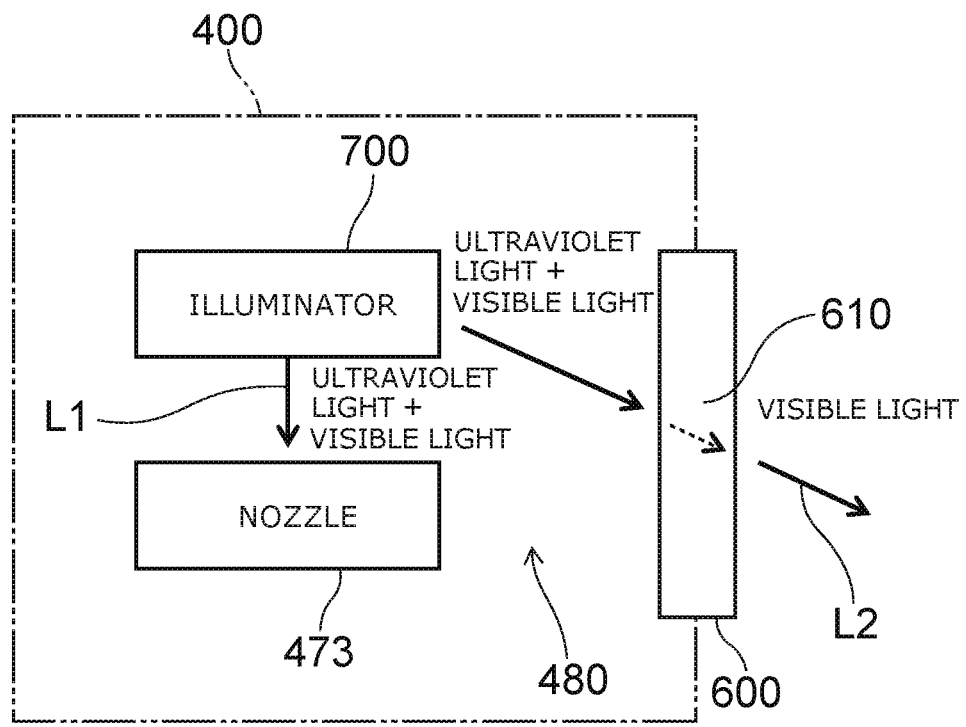

FIG. 15A and FIG. 15B are descriptive views schematically illustrating the illuminator periphery of the sanitary washing device according to the embodiment.

As illustrated in FIG. 15A and FIG. 15B, for example, the illuminator 700 irradiates sterilizing light including an ultraviolet light component. For example, the illuminator 700 is provided in the interior of the casing 400 (inward of the nozzle lid 600). Thus, by irradiating the sterilizing light including the ultraviolet light component from the illuminator 700 provided in the interior of the casing 400, the sterilizing light that includes the ultraviolet light component can be irradiated more reliably into the interior of the nozzle container 480.

As described above, in the case where the nozzle lid 600 includes a wavelength conversion material (e.g., a fluorescent material) that can convert the ultraviolet light component into a visible light component, the illuminator 700 can cause the nozzle lid 600 to be luminous by converting the ultraviolet light component included in the sterilizing light into the visible light component by the nozzle lid 600 as illustrated in FIG. 15A.

Thus, because the nozzle lid 600 includes the wavelength conversion material, the nozzle lid 600 that is positioned outside the nozzle container 480 can be caused to be luminous even when a large clearance for leaking the light is not provided between the nozzle lid 600 and the opening 481 of the nozzle container 480. Thereby, the user can visually be given a real sense that the interior of the nozzle container 480 is being sterilized by the sterilizing light while more reliably suppressing the penetration of urine or the like between the nozzle lid 600 and the opening 481 of the nozzle container 480.

As illustrated in FIG. 15B, the illuminator 700 may irradiate sterilizing light including an ultraviolet light component and a visible light component. Thus, by irradiating the sterilizing light including the ultraviolet light component and the visible light component from the illuminator 700 provided in the interior of the casing 400, the user can perceive that the nozzle container 480 is being sterilized by the sterilizing light even when another illuminator 750 or the like irradiating light including a visible light component is not provided.

In such a case, it is favorable for the nozzle lid 600 to include a transmissive portion 610 that can transmit the visible light component. For example, the transmittance of the transmissive portion 610 for the visible light component is higher than the transmittance of the front surface 400a of the casing 400 for the visible light component. The illuminator 700 can cause the nozzle lid 600 to be luminous by causing the visible light component to pass through the transmissive portion 610.

Thus, because the nozzle lid 600 includes the transmissive portion 610, the visual confirmation effect by the user can be increased by the visible light component included in the sterilizing light irradiated from the illuminator 700 passing through the transmissive portion 610 while increasing the performance of sterilizing the interior of the nozzle container 480 due to the ultraviolet light component included in the sterilizing light irradiated from the illuminator 700.

In the case where the illuminator 700 irradiates the sterilizing light including the ultraviolet light component and the visible light component, by providing the gap (the clearance) between the nozzle lid 600 and the opening 481 of the nozzle container 480 as described above, the sterilizing light that includes the ultraviolet light component and the visible light component irradiated into the interior of the nozzle container 480 from the illuminator 700 may be emitted outside the casing 400 from the gap between the opening 481 and the nozzle lid 600.

Figure 16A:
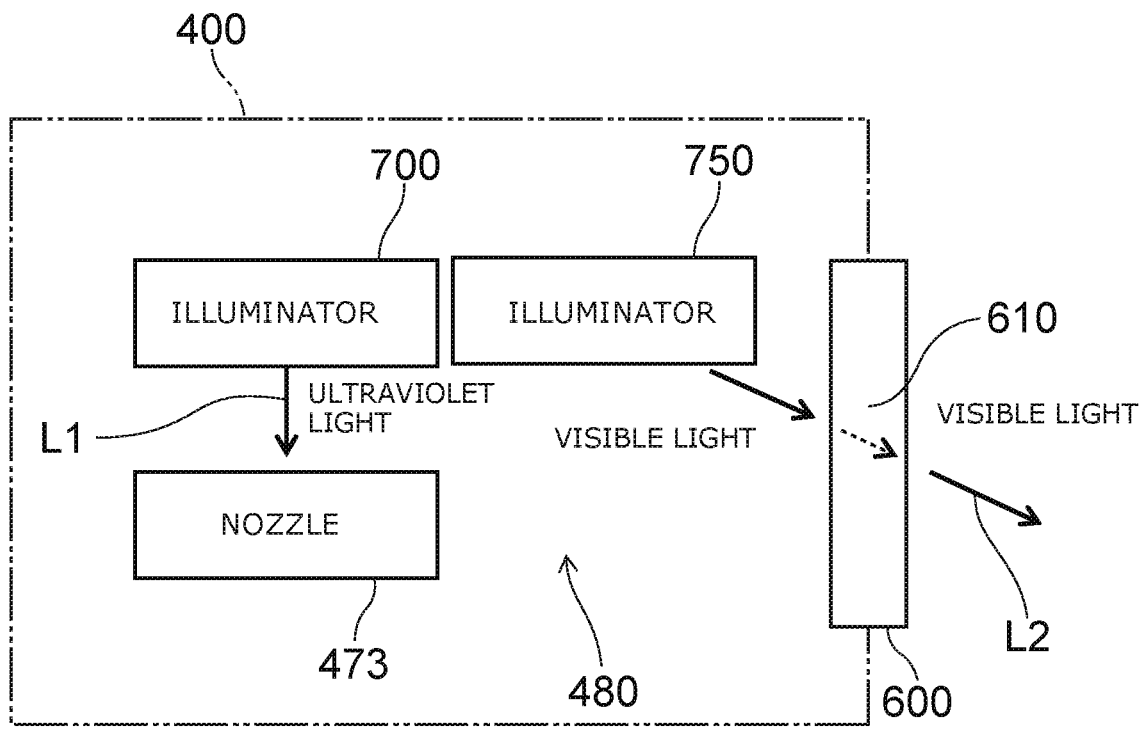
FIG. 16A and FIG. 16B are descriptive views schematically illustrating the illuminator periphery of a modification of the sanitary washing device according to the embodiment.
Figure 16B:
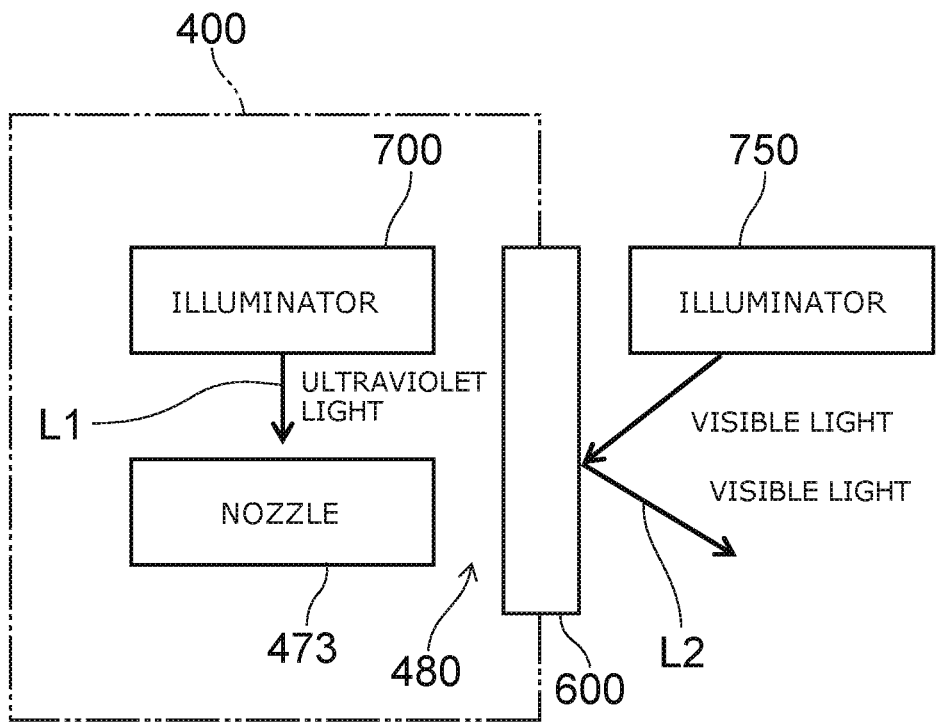

FIG. 16A and FIG. 16B are descriptive views schematically illustrating the illuminator periphery of a modification of the sanitary washing device according to the embodiment.

As illustrated in FIG. 16A and FIG. 16B, the sanitary washing device 100 according to the embodiment may further include another illuminator 750 irradiating light including a visible light component in addition to the illuminator 700 irradiating sterilizing light including an ultraviolet light component.

The illuminator 750 irradiates the light including the visible light component onto at least one of the nozzle lid 600 or the vicinity 650 of the nozzle lid 600 when irradiating the sterilizing light from the illuminator 700 into the interior of the nozzle container 480 when the nozzle lid 600 is in the closed state.

Thus, by providing the other illuminator 750 irradiating the light including the visible light component in addition to the illuminator 700 irradiating the sterilizing light including the ultraviolet light component and by irradiating the light including the visible light component from the illuminator 750 onto at least one of the nozzle lid 600 or the vicinity 650 of the nozzle lid 600 when the sterilizing light is irradiated from the illuminator 700, the user can perceive that the nozzle container 480 is being sterilized by the sterilizing light due to the light including the visible light component irradiated from the illuminator 750 even in the case where the sterilizing light irradiated from the illuminator 700 does not include a visible light component.

The illuminator 750 may be provided in the interior of the casing 400 (inward of the nozzle lid 600) as illustrated in FIG. 16A or may be provided outside the casing 400 (outward of the nozzle lid 600) as illustrated in FIG. 16B.

In the case where the illuminator 750 is provided in the interior of the casing 400 as illustrated in FIG. 16A, it is favorable for the nozzle lid 600 to include the transmissive portion 610 that can transmit the visible light component. The illuminator 750 can cause the nozzle lid 600 to be luminous by causing the visible light component to pass through the transmissive portion 610.

Thus, because the nozzle lid 600 includes the transmissive portion 610, the visual confirmation effect by the user can be increased by the visible light component included in the light irradiated from the illuminator 750 passing through the transmissive portion 610 while increasing the performance of sterilizing the interior of the nozzle container 480 due to the ultraviolet light component included in the sterilizing light irradiated from the illuminator 700.

In the case where the illuminator 750 is provided in the interior of the casing 400, the light that includes the visible light component irradiated from the illuminator 750 may be emitted outside the casing 400 from the gap between the opening 481 and the nozzle lid 600 by providing the gap (the clearance) between the nozzle lid 600 and the opening 481 of the nozzle container 480 as described above.

On the other hand, in the case where the illuminator 750 is provided outside the casing 400 as illustrated in FIG. 16B, it is favorable for the nozzle lid 600 to be configured to reflect the visible light component. Thus, because the nozzle lid 600 is configured to reflect the visible light component, the light that includes the visible light component irradiated from the illuminator 750 provided outside the casing 400 can be reflected by the nozzle lid 600; and the user can perceive that the nozzle container 480 is being sterilized by the sterilizing light.

Thus, in the embodiment, at least one of the illuminator 700 or the illuminator 750 causes at least one of the nozzle lid 600 or the vicinity 650 of the nozzle lid 600 to be luminous in the state of being visible to the user when the sterilizing light from the illuminator 700 is irradiated into the interior of the nozzle container 480 when the nozzle lid 600 is in the closed state; thereby, the user can visually be given a real sense that the interior of the nozzle container 480 is being sterilized by the sterilizing light.

It is favorable for the radiant intensity of the ultraviolet light component to be greater than the radiant intensity of the visible light component in the case where the illuminator 700 irradiates the light including the ultraviolet light component and the visible light component or in the case where the illuminator 700 irradiates the sterilizing light including the ultraviolet light component and the illuminator 750 irradiates the light including the visible light component. Thus, by setting the radiant intensity of the ultraviolet light component to be greater than the radiant intensity of the visible light component, the performance of sterilizing the interior of the nozzle container 480 with the ultraviolet light component can be increased further.

It is favorable for the radiant intensity of light L2 of the at least one of the nozzle lid 600 or the vicinity 650 of the nozzle lid 600 caused to be luminous to be less than the radiant intensity of a sterilizing light L1 irradiated into the interior of the nozzle container 480 from the illuminator 700.

As illustrated in FIG. 15A, FIG. 15B, FIG. 16A, and FIG. 16B, the light L2 of the at least one of the nozzle lid 600 or the vicinity 650 of the nozzle lid 600 caused to be luminous is, for example, fluorescence, transmitted light, reflected light, or the like due to the light irradiated from the illuminator 700 or the illuminator 750. More specifically, for example, the light L2 may be fluorescence produced by the sterilizing light irradiated from the illuminator 700 undergoing wavelength conversion at the nozzle lid 600 including the wavelength conversion material and being emitted outside the nozzle lid 600, may be transmitted light produced by the sterilizing light irradiated from the illuminator 700 or the light irradiated from the illuminator 750 passing through the nozzle lid 600 including the transmissive portion 610, or may be reflected light produced by the light irradiated from the illuminator 750 being reflected by the nozzle lid 600.

Thus, the irradiation on the user of light having a strong sterilizing power can be suppressed by setting the radiant intensity of the light L2 of the at least one of the nozzle lid 600 or the vicinity 650 of the nozzle lid 600 caused to be luminous to be less than the radiant intensity of the sterilizing light L1 irradiated into the interior of the nozzle container 480 from the illuminator 700. Thereby, the performance of sterilizing the interior of the nozzle container 480 can be increased while increasing the safety of the user.

It is favorable for the peak wavelength of the light L2 of the at least one of the nozzle lid 600 or the vicinity 650 of the nozzle lid 600 caused to be luminous to be longer than the peak wavelength of the sterilizing light L1 irradiated into the interior of the nozzle container 480 from the illuminator 700.

Thus, the irradiation on the user of light having a strong sterilizing power can be suppressed by setting the peak wavelength of the light L2 of the at least one of the nozzle lid 600 or the vicinity 650 of the nozzle lid 600 caused to be luminous to be longer than the peak wavelength of the sterilizing light L1 irradiated into the interior of the nozzle container 480 from the illuminator 700. Thereby, the performance of sterilizing the interior of the nozzle container 480 can be increased while increasing the safety of the user.

Hereinabove, embodiments of the invention are described. However, the invention is not limited to these descriptions. Appropriate design modifications made by one skilled in the art for the embodiments described above also are within the scope of the invention to the extent that the features of the invention are included. For example, the configurations, the dimensions, the materials, the arrangements, the mounting methods, etc., of the components included in the sanitary washing device 10, etc., are not limited to those illustrated and can be modified appropriately.

Also, the components included in the embodiments described above can be combined within the limits of technical feasibility; and such combinations are within the scope of the invention to the extent that the features of the invention are included.

What is claimed is:
1. A sanitary washing device, comprising:
a private part wash nozzle having a water discharge port dispensing washing water toward a private part of a user;
a drive device causing the private part wash nozzle to advance and retract;
a casing including a nozzle container configured to store an entirety of the private part wash nozzle in a state in which the private part wash nozzle is retracted;
a nozzle lid provided to be openable and closable with respect to an opening provided at a front end of the nozzle container, the nozzle lid being in an open state in which the opening is open when the private part wash nozzle is advanced, the nozzle lid being in a closed state in which the opening is closed when the entirety of the private part wash nozzle is stored in the nozzle container; and
an illuminator irradiating sterilizing light into an interior of the nozzle container, the sterilizing light having a sterilizing effect,
wherein the illuminator irradiates the sterilizing light including an ultraviolet light component,
wherein the nozzle lid includes a wavelength conversion material configured to convert the ultraviolet light component into a visible light component, and
wherein the illuminator causes the nozzle lid to be luminous by converting the ultraviolet light component into the visible light component at the nozzle lid when the nozzle lid is in the closed state and the sterilizing light from the illuminator is irradiated into the interior of the nozzle container.

2. A sanitary washing device, comprising:
a private part wash nozzle having a water discharge port dispensing washing water toward a private part of a user;
a drive device causing the private part wash nozzle to advance and retract;

a casing including a nozzle container configured to store an entirety of the private part wash nozzle in a state in which the private part wash nozzle is retracted;

a nozzle lid provided to be openable and closable with respect to an opening provided at a front end of the nozzle container, the nozzle lid being in an open state in which the opening is open when the private part wash nozzle is advanced, the nozzle lid being in a closed state in which the opening is closed when the entirety of the private part wash nozzle is stored in the nozzle container; and an illuminator irradiating sterilizing light into an interior of the nozzle container, the sterilizing light having a sterilizing effect, wherein the illuminator irradiates an ultraviolet light component as the sterilizing light and a visible light component, wherein the at least one of the nozzle lid or a vicinity of the nozzle lid is caused to be luminous by utilizing the visible light component when the nozzle lid is in the closed state and the sterilizing light from the illuminator is irradiated into the interior of the nozzle container.

3. The device according to claim 2, wherein the nozzle lid includes a transmissive portion configured to transmit the visible light component, and the illuminator causes the nozzle lid to be luminous by causing the visible light component to pass through the transmissive portion.

4. The device according to claim 2, further comprising an other illuminator irradiating light including a visible light component, the other illuminator irradiating the light including the visible light component on the at least one of the nozzle lid or the vicinity of the nozzle lid when the nozzle lid is in the closed state and the sterilizing light from the illuminator is irradiated into the interior of the nozzle container.

5. The device according to claim 4, wherein the nozzle lid includes a transmissive portion configured to transmit the visible light component, and the other illuminator causes the nozzle lid to be luminous by causing the visible light component to pass through the transmissive portion.

6. The device according to claim 2, wherein a radiant intensity of the ultraviolet light component is greater than a radiant intensity of the visible light component.

7. The device according to claim 1, wherein a radiant intensity of the light from the nozzle lid being caused to be luminous is less than a radiant intensity of the sterilizing light irradiated into the interior of the nozzle container from the illuminator.

8. The device according to claim 1, wherein a peak wavelength of the light from the nozzle lid being caused to be luminous is longer than a peak wavelength of the sterilizing light irradiated into the interior of the nozzle container from the illuminator.

9. The device according to claim 1, wherein the nozzle lid includes a phosphorescent material.

10. The device according to claim 1, further comprising:

a human body detection sensor detecting the user at a vicinity of the sanitary washing device; and a controller controlling the illuminator based on detection information of the human body detection sensor, from a state in which the human body detection sensor does not detect the user, the controller causes the illuminator to operate when the human body detection sensor detects the user.

11. The device according to claim 10, further comprising:

a toilet seat where the user can contact the seat; and a seat contact detection sensor detecting the seat contact of the user on the toilet seat, from a state in which the seat contact detection sensor does not detect the seat contact, the controller stops the operation of the illuminator when the seat contact detection sensor detects the seat contact.

12. The device according to claim 11, wherein the controller operates the illuminator even in the state in which the human body detection sensor does not detect the user.

13. The device according to claim 12, wherein the controller controls the illuminator to cause an operation time of the illuminator in the state in which the human body detection sensor does not detect the user to be longer than an operation time of the illuminator in the state in which the human body detection sensor detects the user.

14. The device according to claim 2, wherein a radiant intensity of the light from the at least one of the nozzle lid or the vicinity of the nozzle lid being caused to be luminous is less than a radiant intensity of the sterilizing light irradiated into the interior of the nozzle container from the illuminator.

15. The device according to claim 2, wherein a peak wavelength of the light from the at least one of the nozzle lid or the vicinity of the nozzle lid being caused to be luminous is longer than a peak wavelength of the sterilizing light irradiated into the interior of the nozzle container from the illuminator.

16. The device according to claim 2, wherein the nozzle lid includes a phosphorescent material.

17. The device according to claim 2, further comprising:

a human body detection sensor detecting the user at a vicinity of the sanitary washing device; and a controller controlling the illuminator based on detection information of the human body detection sensor, from a state in which the human body detection sensor does not detect the user, the controller causes the illuminator to operate when the human body detection sensor detects the user.

18. The device according to claim 17, further comprising:

a toilet seat where the user can contact the seat; and a seat contact detection sensor detecting the seat contact of the user on the toilet seat, from a state in which the seat contact detection sensor does not detect the seat contact, the controller stops the operation of the illuminator when the seat contact detection sensor detects the seat contact.

19. The device according to claim 18, wherein the controller operates the illuminator even in the state in which the human body detection sensor does not detect the user.

20. The device according to claim 19, wherein the controller controls the illuminator to cause an operation time of the illuminator in the state in which the human body detection sensor does not detect the user to be longer than an operation time of the illuminator in the state in which the human body detection sensor detects the user.

* * * * *